United States Patent
Dishon et al.

(10) Patent No.: US 8,482,715 B2
(45) Date of Patent: *Jul. 9, 2013

(54) MONITORING APPARATUS AND METHOD PARTICULARLY USEFUL IN PHOTOLITHOGRAPHICALLY PROCESSING SUBSTRATES

(75) Inventors: Giora Dishon, Jerusalem (IL); Moshe Finarov, Rehovot (IL); Zvi Nirel, Mevaseret Zion (IL); Yoel Cohen, Nes Ziona (IL)

(73) Assignee: Nova Measuring Instruments Ltd., Rehovot (IL)

( * ) Notice: Subject to any disclaimer, the term of this patent is extended or adjusted under 35 U.S.C. 154(b) by 338 days.

This patent is subject to a terminal disclaimer.

(21) Appl. No.: 12/911,371

(22) Filed: Oct. 25, 2010

(65) Prior Publication Data
US 2011/0037957 A1 Feb. 17, 2011

Related U.S. Application Data

(63) Continuation of application No. 12/429,017, filed on Apr. 23, 2009, now Pat. No. 7,821,614, which is a continuation of application No. 11/924,365, filed on Oct. 25, 2007, now Pat. No. 7,525,634, which is a continuation of application No. 11/402,009, filed on Apr. 12, 2006, now Pat. No. 7,289,190, which is a continuation of application No. 10/763,383, filed on Jan. 26, 2004, now Pat. No. 7,030,957, which is a continuation of application No. 09/730,919, filed on Dec. 6, 2000, now Pat. No. 6,842,220, which is a continuation of application No. 09/184,727, filed on Nov. 2, 1998, now Pat. No. 6,166,801.

(30) Foreign Application Priority Data
Jul. 14, 1998 (IL) .......................................... 125337

(51) Int. Cl.
G03B 27/32 (2006.01)
G01B 11/00 (2006.01)
G01N 21/00 (2006.01)

(52) U.S. Cl.
USPC .......................... 355/27; 396/611; 356/237.2

(58) Field of Classification Search
USPC ...... 355/27, 52, 53, 55, 67; 356/237.2–237.5, 356/394; 396/578, 611; 430/30
See application file for complete search history.

(56) References Cited

U.S. PATENT DOCUMENTS
4,308,586 A 12/1981 Coates
4,328,553 A 5/1982 Fredriksen et al.
(Continued)

FOREIGN PATENT DOCUMENTS
EP 0 456 479 A2 11/1991
EP 0 793 147 A1 9/1997
(Continued)

OTHER PUBLICATIONS
Ausschnitt C.P. et al., "Seeing the Forest of Trees: A New Approach to CD Control", SPIE. 1998, vol. 3332, 212-220.

*Primary Examiner* — Hung Henry Nguyen
(74) *Attorney, Agent, or Firm* — Browdy and Neimark, PLLC

(57) ABSTRACT

A system for determining at least two properties of a substrate, including a supporting plate configured to support the substrate, and a measurement device coupled to the supporting plate, including an illumination system configured to direct light toward a surface of the substrate, and a detection system coupled to the illumination system and configured to detect light propagating from the surface of the substrate, wherein the measurement device is configured to generate one or more output signals in response to the detected light, and a control unit coupled to the measurement device and configured to determine a first property and a second property of the substrate from the one or more output signals, wherein the first property comprises a presence of macro defects on the substrate, and wherein the second property comprises overlay misregistration in the substrate.

20 Claims, 15 Drawing Sheets

U.S. PATENT DOCUMENTS

| | | | |
|---|---|---|---|
| 4,475,122 | A | 10/1984 | Green |
| 4,516,855 | A | 5/1985 | Korth |
| 4,555,767 | A | 11/1985 | Case et al. |
| 4,585,348 | A | 4/1986 | Chastang et al. |
| 4,595,289 | A | 6/1986 | Feldman et al. |
| 4,618,262 | A | 10/1986 | Maydan et al. |
| 4,647,207 | A | 3/1987 | Bjork et al. |
| 4,653,924 | A | 3/1987 | Itonaga et al. |
| 4,681,450 | A | 7/1987 | Azzam |
| 4,713,140 | A | 12/1987 | Tien |
| 4,815,856 | A | 3/1989 | Bruce |
| 4,826,321 | A | 5/1989 | Coates et al. |
| 4,842,410 | A | 6/1989 | Darrah et al. |
| 4,873,430 | A | 10/1989 | Juliana et al. |
| 4,900,939 | A | 2/1990 | Aoyama |
| 4,908,508 | A | 3/1990 | Dubbeldam |
| 4,910,549 | A | 3/1990 | Sugita |
| 4,957,368 | A | 9/1990 | Smith |
| 4,974,919 | A | 12/1990 | Muraki et al. |
| 4,999,014 | A | 3/1991 | Gold et al. |
| 5,042,951 | A | 8/1991 | Gold et al. |
| 5,061,072 | A | 10/1991 | Folkard et al. |
| 5,109,430 | A | 4/1992 | Nishihara et al. |
| 5,120,966 | A | 6/1992 | Kondo |
| 5,159,412 | A | 10/1992 | Willenborg et al. |
| 5,166,752 | A | 11/1992 | Spanier et al. |
| 5,181,080 | A | 1/1993 | Fanton et al. |
| 5,274,575 | A | 12/1993 | Abe |
| 5,333,052 | A | 7/1994 | Finarov |
| 5,393,624 | A | 2/1995 | Ushijima |
| 5,420,680 | A | 5/1995 | Isobe et al. |
| 5,438,209 | A | 8/1995 | Yamamoto et al. |
| 5,438,413 | A | 8/1995 | Mazor et al. |
| 5,604,344 | A | 2/1997 | Finarov |
| 5,682,242 | A | 10/1997 | Eylon |
| 5,695,564 | A | 12/1997 | Imahashi |
| 5,825,913 | A | 10/1998 | Rostami et al. |
| 5,826,129 | A | 10/1998 | Hasebe et al. |
| 5,872,632 | A | 2/1999 | Moore |
| 5,877,036 | A | 3/1999 | Kawai |
| 5,963,753 | A | 10/1999 | Ohtani et al. |
| 6,004,047 | A | 12/1999 | Akimoto et al. |
| 6,038,029 | A | 3/2000 | Finarov |
| 6,064,477 | A | 5/2000 | Matsumoto et al. |
| 6,100,985 | A | 8/2000 | Scheiner et al. |
| 6,166,801 | A | 12/2000 | Dishon et al. |
| 6,266,125 | B1 | 7/2001 | Fukuda et al. |
| 6,424,417 | B1 | 7/2002 | Cohen et al. |
| 6,603,529 | B1 | 8/2003 | Finarov |
| 6,643,017 | B2 | 11/2003 | Cohen et al. |
| 6,842,220 | B1 | 1/2005 | Dishon et al. |
| 7,030,957 | B2 | 4/2006 | Dishon et al. |
| 7,289,190 | B2 | 10/2007 | Dishon et al. |
| 7,525,634 | B2 * | 4/2009 | Dishon et al. .............. 355/27 |
| 7,589,832 | B2 * | 9/2009 | Den Boef et al. ......... 356/237.2 |
| 2002/0033450 | A1 | 3/2002 | Finarov et al. |
| 2011/0128512 | A1 * | 6/2011 | Pellemans et al. ............ 355/27 |

FOREIGN PATENT DOCUMENTS

| | | |
|---|---|---|
| EP | 0 558 781 B1 | 8/1998 |
| JP | 59 125009 A | 7/1984 |
| JP | 01 054207 A | 3/1989 |
| WO | WO 02/25723 A2 | 3/2002 |

* cited by examiner

MONITORING APPARATUS AND METHOD PARTICULARLY USEFUL IN PHOTOLITHOGRAPHICALLY PROCESSING SUBSTRATES

CROSS-REFERENCE TO RELATED APPLICATIONS

The present application is a continuation of parent application Ser. No. 12/429,017, filed Apr. 23, 2009 (now U.S. Pat. No. 7,821,614), which is a continuation of parent application Ser. No. 11/924,365, filed Oct. 25, 2007 (now U.S. Pat. No. 7,525,634), which is a continuation of parent application Ser. No. 11/402,009, filed Apr. 12, 2006 (now U.S. Pat. No. 7,289,190), which is a continuation of U.S. application Ser. No. 10/763,383, filed Jan. 26, 2004 (now U.S. Pat. No. 7,030,957), which is a continuation of U.S. application Ser. No. 09/730,919, filed Dec. 6, 2000 now U.S. Pat. No. 6,842,220, which is a continuation of U.S. application. No. 09/184,727 (now U.S. Pat. No. 6,166,801), filed Nov. 2, 1998, and claiming priority from Israel application No. 125337, filed Jul. 14, 1998. The entire contents of which is hereby incorporated by reference.

FIELD OF THE INVENTION

The present invention relates to inspection apparatus and methods particularly useful in photolithographically processing substrates. The invention is especially useful in producing semiconductors, and is therefore described below with respect to this application.

BACKGROUND OF THE INVENTION

The principal process of semiconductor production is photolithography, which includes three main serial steps or operations:
(a) coating the wafer with photoresist material (PR);
(b) exposing the PR through a mask with a predetermined pattern in order to produce a latent image of the mask on the PR; and
(c) developing the exposed PR in order to produce the image of the mask on the wafer.

The satisfactory performance of these steps requires a number of measurement and inspection steps in order to closely monitor the process.

Generally speaking, prior to a photolithography process, the wafer is prepared for the deposition of one or more layers. After a photolithography process is completed, the uppermost layer on the wafer is etched. Then, a new layer is deposited in order to begin the aforementioned sequence once again. In this repetitive way, a multi-layer semiconductor wafer is produced.

FIG. 1 schematically illustrates a typical set-up of photocluster tools of the photolithography process in a semiconductor fabrication plant (Fab). The photocluster (or link) is composed of two main parts: the phototrack 5, and the exposure tool 8. The phototrack includes a coater track 6 having a cassette load station 6a, and a developer track 10 having a cassette unload station 10a. Alternatively, both coater and developer functions may be combined and realized in the same stations (not shown). The wafer W is placed in the cassette station 6a. From there the wafer is loaded by a robot 2 to the coater track 6 where the coating step (a) commences. After step (a), the wafer is transferred by the robot 2 to the exposure tool 8, where the exposing step (b) is executed. Here, using optical means installed inside the exposure tool, the pattern on the mask is aligned with the structure already on the wafer (registration). Then, the wafer W is exposed to electromagnetic radiation through the mask. After exposure, robot 2 transfers the wafer to the developer track 10 where the micro-dimensional relief image on the wafer is developed (step). The wafer W is then transferred by robot 2 to the cassette station 10a. Steps (a)-(c) also involve several different baking and other auxiliary steps which are not described herein.

As shown in FIG. 1, the coater track 6, the exposure tool 8, and the developer track 10, are tightly joined together in order to minimize process variability and any potential risk of contamination during photolithography, which is a super-sensitive process. Some available commercial exposure tools are series (MA-1000, 200, 5500) of Dainippon Screen MFG. Co. Ltd., Kyoto, Japan, PAS-5500 series of ASM Lithography, Tempe, Ariz., series FPA 3000 and 4000 of Canon USA Inc., USA, and Microscan of SVGL, Wilton, Conn. Some available phototracks are series 90s and 200 of SVGT, San-Jose, Calif., Polaris of FSI International, Chaska, Minn., and phototracks D-spin series (60A/80A, 60B, 200)) of Dainippon Screen MFG. Co. Ltd., Kyoto, Japan, Falcon of Fairchild Technologies Inc., USA and of Tokyo Electric Laboratories (TEL), Japan.

It is apparent that in such a complex and delicate production process, various problems, failures or defects, may arise or develop during each step, or from the serial combination of steps. Because of the stringent quality requirements, any problem which is not discovered in time may result in the rejection of a single wafer, or of the whole lot.

A wafer cannot be taken out of the photocluster for measurement or inspecting before the process is completed and the wafer arrives at the cassette station 10b. As a result, any process control based on measuring processed wafers cannot provide 'real time' process malfunction detection. Therefore, there is an urgent need for an approach based on integrated monitoring, i.e., a monitoring apparatus physically installed inside or attached to the relevant production unit, dedicated to it, and using its wafer handling system. Such integrated monitoring can provide tight, fast-response and accurate monitoring of each of the steps, as well as complete and integrated process control for the overall semiconductor production process, in general, and for photolithography, in particular.

However, examination of the prior art, insofar as known to us, indicates that no such monitoring and control methods and/or systems exist. Rather, only 'stand-alone' monitoring systems appear to be available at the moment.

A 'Stand-alone' monitoring system is one which is installed outside the production line and in which the wafers are transferred from the production unit to the monitoring system using a separate handling system than that of the production process.

In general, three different monitoring and control processes are performed at the present time during semiconductor fabrication process. These are monitoring of (a) overlay misregistration, (b) inspecting and (c) critical dimension (CD) measurement. A brief description of each of these processes is given below:

(a) Overlay Registration Control

The overlay registration (hereinafter—"overlay") is a process executed in the exposure tool 8 in which the pattern on the mask is aligned with respect to the pattern features existing already on the uppermost layer on the wafer. The shrinking dimensions of the wafer's features increases the demands on overlay accuracy.

An overlay error or misregistration (hereinafter—"overlay error") is defined as the relative misalignment of the features produced by two different mask levels. The error is determined by a separate metrology tool from the exposure tool.

FIG. 2(a) illustrates a typical overlay error determination site on a wafer. It is composed of two groups of target lines, one on the uppermost feature layer of the wafer 11 and the second is produced on the new PR layer 16. Target lines 16 are similar but smaller than target lines 11; thus they can be placed in the center of target lines 11. Therefore, these overlay targets are called "bars in bars". FIG. 2(b) is a top view of the same overlay error determination site. The lines of these targets, such as 11a and 16a are typically of ~2 μm width, and 10-15 μm length, respectively.

According to a common method, the overlay error is defined as the relative displacement of the centers of target lines 11 with respect to lines 16, in both the x and y axis. For example, in FIG. 6 the displacements between lines 11a and 16a, 11b and 16b are denoted as 14a and 14b, respectively. Thus, the overlay error in the x axis is the difference between the lengths of lines 14a and 14b.

FIG. 3 illustrates a common configuration of photocluster tools and a 'stand-alone' overlay metrology system composed of a measurement unit and an analysis station. It should be noted that wafers to be examined are taken out of the photo-litography process-line, and handled in the measurement tool. The latter results from the facts that with the available overlay technology (i): closed loop control in 'real time' is not possible; (ii) not all the wafers as well as all the layers within a wafer are measured for overlay error; (iii) additional process step is needed; and (iv) a 'stand alone' tool is needed. It should be noted that it is a common situation in the Fab, especially in advanced production processes, that during 'stand alone' overlay measurement, the processing of the lot is stopped. This break may even take a few hours.

The results of the measurements are sent to the analysis station, and a feedback is returned to the stepper in the photocluster tool.

U.S. Pat. No. 5,438,413 discloses a process and a 'stand-alone' apparatus for measuring overlay errors using an interferometric microscope with a large numerical aperture. A series of interference images are that different vertical planes, and artificial images thereof are processed, the brightness of which is proportional to either the complex magnitude or the phase of the mutual coherence. The differences between synthetic images relating to target attribute position are then used as a means of detecting overlay error. KLA-Tencor, Calif., the assignee of this patent, sells a 'stand-alone' machine under the brand name KLA-5200. In this system, the measurement and the analysis station are combined together.

U.S. Pat. No. 5,109,430 discloses another overlay metrology system. By comparing spatially filtered images of patterns taken from the wafer with stored images of the same patterns, the overlay error is determined. Schlumberger ATE, Concord, Mass., the assignee of this patent, supplies a 'stand-alone' machine for submicron overlay under the brand name IVS-120.

Other 'stand-alone' overlay metrology systems are manufactured by BIO-RAD micromeasurements, York, Great Britain, under the brand name Questar Q7, as well as by Nanometrics, Sunnyvale, Calif. (Metra series).

All the aforementioned methods and metrology systems for determining overlay error suffer from several drawbacks including the following:

1) They are all 'stand-alone' systems, i.e., operating off-line the photolithography process. Thus, they provide post-process indication of overlay errors, not during the production process itself, or before a batch of wafer production is completed. In some cases this may take hours, or more.

2) They result in a waste of wafers, and/or lots of wafers because of this post-process response. This results from the continuous operation of the photolithographic process on the one hand, and the time-delay from the time a wafer is sent offline to overlay measurements until a response about an error is obtained, on the other hand.

3) Usually, one of the main overlay error sources is the first mask alignment for a wafer to come on a lot. Such an error source cannot be corrected later since the error varies for each lot. For this reason it is important to have the feedback within the time frame of the first wafer which cannot be obtained using a 'stand-alone' tool.

4) The overlay sampling frequency is limited due to contamination restrictions and additional expensive time needed for extra handling and measurements.

5) Throughput of the photolithography process is reduced as a result of the post-process overlay detection and the long response-time, as well as of the reduced sampling frequency mentioned in (3).

6) These stand-alone systems require additional expensive foot-print and labor in the Fab.

7) The microlithography tools are the "bottle neck" in the semiconductors production process and they are the most expensive tools in the FAB. Their partial utilization due to late off-line measurements reduces drastically overall equipment efficiency in the Fab.

(b) Inspecting

Inspecting during the production of semiconductors wafers can be defined as a search for defects caused by:
(a) contamination (dirt, particles, chemicals, residues, etc.), and/or
(b) process induced failures related to PR, coating, baking, development, handling, etc.

In order to detect defects originating only from the lithography process, a specific inspecting step is conducted after the development step as illustrated in FIG. 4. It is usually called "after development inspecting" (ADI), or "post-development check" (PDCK). The present invention is mainly relevant for ADI.

In general, data obtained during the inspecting is analyzed, and in case an increased defects level is detected, an alarm is sent to the engineering level or to the production line. Once again it should be noted that, as in the case of overlay metrology, with the current technology, the ADI is located out of the production line; i.e., wafers to be inspected are taken out of the production process and handled in a separate inspecting station. It should also be noted that it is a common situation in the Fab, especially in advanced production processes, that during 'stand alone' inspecting, the processing of the lot is stopped. This break may take even few hours.

Today, the majority of ADI activities are non-automatic visual inspecting conducted by humans. In particular, no integrated automatic ADI system is commercially available at the moment.

ADI is aimed at:
(i) Coarse inspecting—A wafer is handled by hands and is visually inspected by eye-sight for large defects. These defects can be, for example, poor spinning during coating, poor development, scum, non-attached PR ('lifting'), and/or edge beads. This method can usually only detect defects bigger than tens of microns.
(ii) Fine inspecting—predetermined sites or targets on a wafer are visually inspected with the aid of a microscope (20-50× magnification).

These defects can be, e.g., shorts between conducting lines, and focus failures of the stepper.

ADI conducted by humans has several disadvantages:

(a) It is tedious and requires great concentration to locate pattern discrepancies in repetitive and complex circuits.

(b) The results are not uniform with respect to each inspector as well as between different inspectors. This point becomes crucial when considering the increased importance of inspecting at times when the wafer features become more and more delicate due to the continuous shrinking of the wafer's features.

(c) It is not a consistent means for statistical analysis and for measuring process quality due to non-repetitive results.

(d) Additional costs due to the labor.

(e) Non objective inspecting, neither in defects identification nor in the specific action which should take place once a specific defect is identified.

(f) Fluctuating throughput results, among other things, in difficulties to determine sampling frequency.

(g) Manual inspecting is also done off-line and therefore suffers from all the same aforementioned disadvantages of 'stand-alone' systems.

To complete the picture, it should be noted that two automatic optical inspection (AOI) methods for defect detection are known, but their high cost and low throughput limit their use in actual production.

(i) Absolute methods—illuminating a wafer at a predetermined angle ("grazing") and collecting the reflected signal from the wafer's plane. Any signal above a threshold (absolute) value is determined as a defect. According to this method, particles bigger than 0.1 µm can be detected.

(ii) Comparative methods—these are divided into 'die to die' and 'die to database'. A wafer is photographed and then an automatic comparison of pixels in one die is made with respect to the correlative pixels in a neighbor die, or to a database. Usually, the result of the comparison should fit a set threshold, unless there is a defect. The threshold may be a function of the gray level and/or the specific location of the dye in the wafer.

Method (ii) overcomes the shortcomings of method (i), and usually detects defects such as dirt particles (>0.1 µm), bridging of conducting lines, missing features, residues of chemicals and PR, etc. The defect level these methods can detect is determined according to the design rule of the industry (e.g., 0.1 µm).

None of the available inspecting tools samples each wafer, but only several wafer in a lot. Moreover, the lack of such inspecting systems prevents any option for automatic and tight feedback or closed loop control over the lithography process. Thus, any serious attempt for establishing or even improving the process control around the photolithography process is prevented, or at least is met with crucial obstacles due to the lack of such method(s) and systems.

Critical Dimension (CD) Control

A third monitoring and control process is the Critical Dimension CD control which includes measurements of characteristic dimensions in critical locations on a wafer, e.g., widths of representative lines, spaces, and line/space pairs on the wafer. CD metrology tools are based on two main technologies: the CD scanning electron microscope (CD SEM), and the atomic forced microscope (CDAFM). Commercial tools based on CD SEM are series 7830XX of Applied Materials, Santa Clara, Calif., and DEKTAK SXM-320 of VEECO, USA is based on AFM.

FIG. 5 illustrates common configurations of 'stand-alone' CD tools with the production process. Typically, CD measurements take place after the developing step and/or after etching. The CD tool is located out of the production line, i.e., wafers to be measured are taken out of the production process and handled to a separate CD station. It should be noted that it is a common situation in the Fab, especially in advanced production processes, that during 'stand alone' CD measurement, the processing of the lot is stopped. This break may take even few hours.

In general, data obtained during the CD measurement is analyzed, and then a kind of feedback (or alarm in a case of a width out of the permitted range) is sent to the relevant unit in the production line.

CDSEM and CDAFM allow CD measurement for line/space width below the resolution limit of optical microscope. However, when possible, optical CD (OCD) measurement may be very useful because they can be combined with optical overlay measurement systems. Recently, (C. P. Ausschnitt, M. E., Lagus (1998) Seeing the Forest for the Trees: a New Approach for CD Control", SPIE, vol. 3332, 212-220), it was proposed to use OCD even for sub-micron design rules that is behind the optical resolution. The idea is that optical systems allow fast measurement of many lines simultaneously. Statistical treatment of multiple measurements with low accuracy, allows to extract such important manufacturing data as repeatability or deviation trends.

It is clear, as was noted before with respect to overlay metrology and inspecting tools, that since all CD metrology systems are 'stand-alone' tools, they suffer from the same drawbacks as discussed before. Moreover, especially in the case of CD measurement, the results, e.g., line width, give a limited ability to correlate the measurement to any specific cause.

Methods for Process Control in Lithography

Overlay and CD monitoring can be performed in various levels in order to establish process control. The first common level is "lot to lot control". In this method each lot is a basis for the next lot to run in this process. Small correction can be made by considering the results of the previous lot and making corrections. However a certain increment in the risk is introduced because a total lot may be lost.

A second control level is "send ahead wafer". In this method a pilot wafer is sent through the coating-exposure-developing steps, exposed in the recommended exposure, and is then sent to CD measurement. Satisfactory results will be a basis for the set up conditions of the lot, whereas unsatisfactory results will cause another wafer to be exposed with corrections for the exposure conditions. The over all sequence of a "send ahead wafer" control can take many hours while valuable utility time of the production tools, as well as the production lot, may be lost.

In some cases there is a need for a higher control level. This may be performed in a full process window mapping by running an exposure matrix, or focus exposure matrix, and analyzing the results. However, this is the most time-consuming method.

The drawbacks of these methods, when conducted with 'stand-alone' overlay and OCD tools, are that they are time and effort consuming and they usually do not respond directly for certain causes, or do not reveal any problematic sources. However, they make the "time to respond" shorter as compared to long-term trend charts. Nonetheless, to enable a real feedback to problems, there is a crucial need for integrated monitoring of the process steps. The on-line measurements can respond directly to a certain cause with the correct straight forward correction action.

It should be emphasized that these problems with respect to process control 'stand-alone' systems are dramatically aggravated when considering the coming future developments in the semiconductor industry. Because of the shrinking critical dimensions of the wafer's features, as well as the introduction of new and non-stable processes (e.g., DUV resist, and transition to 300 mm diameter wafer with corresponding restrictions on wafer handling), the need for an integrated monitoring and process control for semiconductors production becomes crucial. For this reason, traditional process control methods that use long-term trend charts, and which are "offline methods" will be more and more excluded.

As noted before, integrated monitoring and process control systems are a reasonable solution for the above discussed problem. However, such a system should be considered from several aspects and meet specific requirements in order to become real and feasible:

(a) Small footprint—such a system should have as small footprint as possible (practically not smaller than the wafer size) in order to be physically installed inside the photocluster;

(b) Stationary wafer—the wafer should be stationary during inspection and measurement to exclude extra wafer-handling;

(c) High throughput—the system should have high throughput such as not to reduce the photocluster throughput;

(d) Cleanliness—the measuring unit should not interfere in any way with the photocluster or introduce any potential risk of contamination;

(e) Access for maintenance—the system parts except the measuring unit (e.g., control electronics, light source), should be outside the photocluster in order to enable, among other things, easy and quick maintenance without any disturbance to the photocluster;

(f) Cost-effective—the integrated tool cost should be a small portion of the phototrack cost;

"Stand-alone" monitoring and process control systems do not meet these stringent requirements, and apparently cannot be used as an integrated system. Moreover, no such integrated system is now available on the market. Therefore, there is a need for a new monitoring and process control apparatus and method having advantages in the above respects.

OBJECTS AND BRIEF SUMMARY OF THE PRESENT INVENTION

An object of the present invention is to provide a novel apparatus and method having advantages in one or more of the above-described respects, particularly important in the photolithography processing of substrates, e.g., semiconductors wafers.

According to one aspect of the present invention, there is provided apparatus for processing substrates according to a predetermined photolithography process, comprising: a loading station in which the substrates are loaded; a coating station in which the substrates are coated with a photoresist material; an exposing station in which the photoresist coating is exposed to light through a mask having a predetermined pattern to produce a latent image of the mask on the photoresist coating; a developing station in which the latent image is developed; and an unloading station in which the substrates are unloaded; characterized in that said apparatus further comprises a monitoring station for monitoring the substrates with respect to predetermined parameters of said photolithography process before being unloaded at the unloading station.

As will be described more particularly below, the optical inspection system between the developing station and the unloading station may detect one or more of the following: (a) overlay registration errors; (b) defects in the photoresist layer; and/or (c) critical dimensional errors.

According to further features in the described preferred embodiments, the inspecting station includes: a supporting plate between the developing station and the unloading station for receiving substrates to be inspected; a sealed enclosure between the developing station and the unloading station and having a transparent window aligned with and facing the supporting plate; an optical inspecting system within the sealed enclosure for inspecting substrates on the supporting plate via said transparent window; and a light source for illuminating the substrates via the optical inspecting system.

In the described preferred embodiments, the light source is externally of the sealed enclosure and produces a light beam which is applied to the optical system within the sealed enclosure.

In addition, the optical inspection system within the sealed enclosure includes an optical image device; and the inspecting station further includes a digital image processing unit externally of the sealed enclosure and connected to the optical imaging device by electrical conductors passing into the sealed enclosure.

The inspecting station further includes a central processing unit externally of the sealed enclosure and connected to the optical inspecting system for controlling the system via electrical conductors passing into the sealed enclosure.

According to still further features in the described preferred embodiments, the optical inspecting system within the sealed enclosure includes: a low-magnification channel for aligning the optical inspecting system with respect to a patterned substrate on the supporting plate or for coarse inspection; and a high-magnification or high-resolution channel for measuring the predetermined parameters of the photolithography process after the substrate has passed through the developing station and before reaching the unloading station. The low-magnification channel and the high-resolution channel are fixed with respect to each other.

The invention also provides a novel method of processing substrates according to a predetermined photolithography process having advantages in the above respects.

As will be described more particularly below, the invention permits one or more or the following to be provided:

1) An integrated apparatus for overlay metrology and/or inspecting. and/or OCD measurements. Such a system would have high accuracy and high throughput and could be physically combined inside the present foot-print of photocluster tools; i.e., it would have a zero additional foot print on the production floor. The combination of up to three different functions in one tool would have its own advantages: (i) Better exploitation of utilization time—each inspecting, overlay and CD measurement could have its own sampling frequency and need not be the same for every wafer. Thus, such a system could be continuously operated while its utilization time is shared between the three functions. (ii) A direct result from (i) is that the system could drastically decrease the numbers of lots which would be simultaneously running around the production process as common today (one for overlay measurement, one for inspecting, one for CD, and one which begins the lithography process), (iii) Such apparatus could be client-oriented, i.e., could be exactly fitted to the customer needs as well as to changing needs. (iv) The system could be oriented for a specific problem; (v) The system could have a relatively low price;

2) An apparatus as in (1) which will not reduce the throughput of the photocluster by carrying out measurements/inspection in parallel with the processing of the next wafer.

3) A modular apparatus as in (1) capable to perform only overlay metrology or inspecting or OCD measurements with enhanced performance if needed.

4) An apparatus as in (1) combined with a processing unit, thus enabling to establish monitoring and process control based on overlay, inspecting and OCD measurements.

5) An integrated automatic inspecting system which is much more accurate, faster, and repetitive than visual inspecting conducted by humans.

6) A method for integrated monitoring and process control for overlay metrology and/or inspecting and/or OCD within the photolitography production process, thereby enabling much shorter response times as compared to the common 'stand-alone' systems.

7) Methods which facilitate and dramatically shorten the time needed for common process control methods such as 'send a wafer ahead', 'lot to lot', etc.

8) A new and practical monitoring and process control method by means of 'wafer to wafer'. Such a method is practically impossible to conduct in the current situation of 'stand-alone' systems. However, with these new integrated methods, which do not decrease the throughput of the production process a tight, fast-responding, directly to cause, monitoring and process control method can be conducted. Apparently, in a certain circumstances these new method may save the need for separate and expensive 'stand-alone' systems for overlay metrology, inspecting and OCD.

9) A method with which both overlay error, inspecting and OCD can be determined either on one wafer of a lot or on different wafers in the same lot.

10) An integrated and elaborated inspecting monitoring and control system.

1. The process can be implemented in several alternative levels. One would be aimed at notifying the production process controller about defects in general. Another would be aimed at investigating the direct reasons and/or the induced failure which caused the defects. Then, a feedback would be directed, to any predetermined relevant point in the production process. By this, a feedback or a closed loop control can be established either for a single step in the production process (e.g., exposure step, post exposure bake (PEB)) or for the whole process when combined with other metrology system(s), such as overlay and/or critical dimension metrology systems.

Such a method and apparatus have the potential to save expensive utilization time (e.g., by shortening methods such as 'send a wafer ahead') as well as diminishing the amount of test wafers wasted during the production process.

In addition, there would be no need for additional wafer handling from or to the photolithography tools, thus saving utilization time as well as preventing additional contamination and wafer breakage.

BRIEF DESCRIPTION OF THE DRAWINGS

The invention is herein described, by way of example only, with reference to the accompanying drawings, wherein.

DETAILED DESCRIPTION OF PREFERRED EMBODIMENTS

Figure 1:
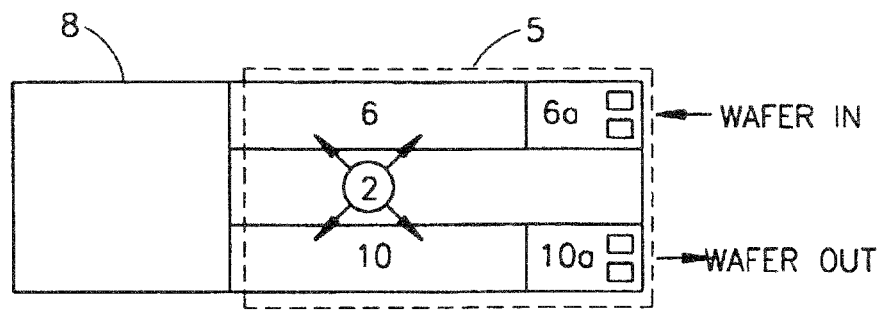
FIG. 1 is typical apparatus set-up of photocluster tools as presently used in a photolithography process of a semiconductor fabrication plant.
Figure 6:
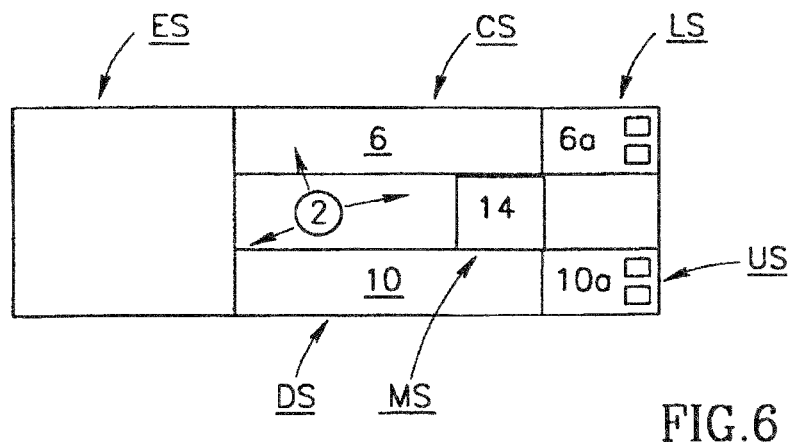
FIG. 6 is a schematic illustration of one manner in which the photolithography cluster tools in the apparatus of FIG. 1 may be combined with an integrated overlay/inspecting/OCD tool in accordance with the present invention.

FIG. 6 schematically illustrates an apparatus set-up corresponding to the conventional one illustrated in FIG. 1 but modified to incorporate an integrated lithography monitoring (ILM) system in accordance with the present invention.

Thus, FIG. 6 illustrates apparatus for processing substrates, in this case wafers w, according to a predetermined photolithography process. This illustrated apparatus comprises: a loading station LS corresponding to the cassette loading station 6*a* in FIG. 1, in which the cassettes are loaded onto the phototrack 5; a coating station CS, corresponding to coater track 6 in FIG. 1 in which the wafers are coated with a photoresist material; an exposure station ES, occupied by the exposure tool 8 in FIG. 1, in which the photoresist coating is exposed to light through a mask having a predetermined pattern to produce a latent image of the mask on the photoresist coating; a developing station DS, corresponding to developer track 10 in FIG. 1, in which the latent image is developed; and an unloading station US, corresponding to station 10*a* in FIG. 1, in which the cassettes are unloaded.

In accordance with the present invention, the apparatus illustrated in FIG. 6 is modified to include a monitoring station MS preferably between the developing station DS and the unloading station US. The monitoring station MS is occupied by an optical monitoring system, generally designated 14 in FIG. 6, which is an ILM (integrated lithography monitoring) system, for measuring and/or inspecting the wafers w with respect to predetermined parameters of the photolithography process after the wafers have passed through the developing station DS and before reaching the unloading station US.

Figure 2A:
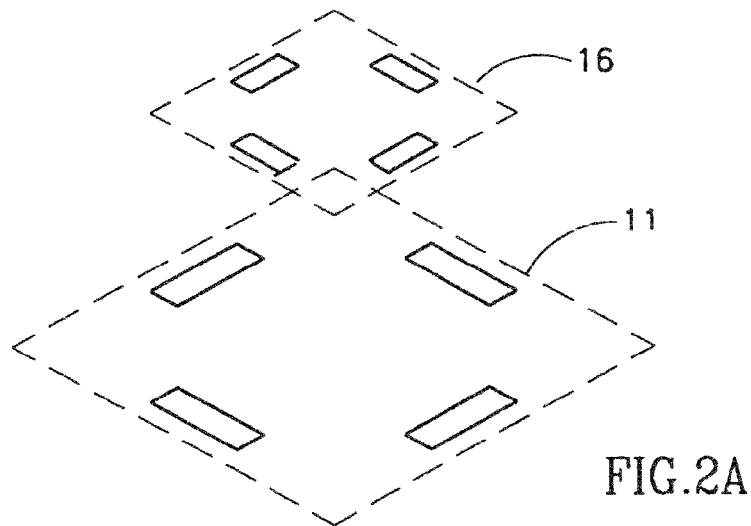
FIGS. 2A and 2B are schematic illustrations of an overlay target.

As will be described more particularly below, the ILM system 14 inspects the wafers w, immediately after processing, for one or more of the following conditions after the wafers have passed through the developing station DS and before reaching the unloading station US; (1) overlay registration errors, in the alignment of the developed image produced on the wafer in the respective photolithography process with respect to a developed image produced on the wafer in a preceding photolithography process performed on the wafer, as described above in FIGS. 2a and 2b; (2) defects in the substrate, induced by the process malfunctions, as well as dirt particles, etc., as described above; and/or (3) critical dimension errors in the developed image of the photoresist coating process produced during the respective photolithography process, as also described above. Preferably, the ILM system 14 performs all three of the above functions, but in some applications, it may detect only one or two or the above type errors.

The exact location of the ILM system 14 in the photocluster is governed by local considerations and circumstances, e.g., on the specific photocluster tool manufacturer, the available foot-print inside the phototrack, and the Fab considerations.

Figure 7:
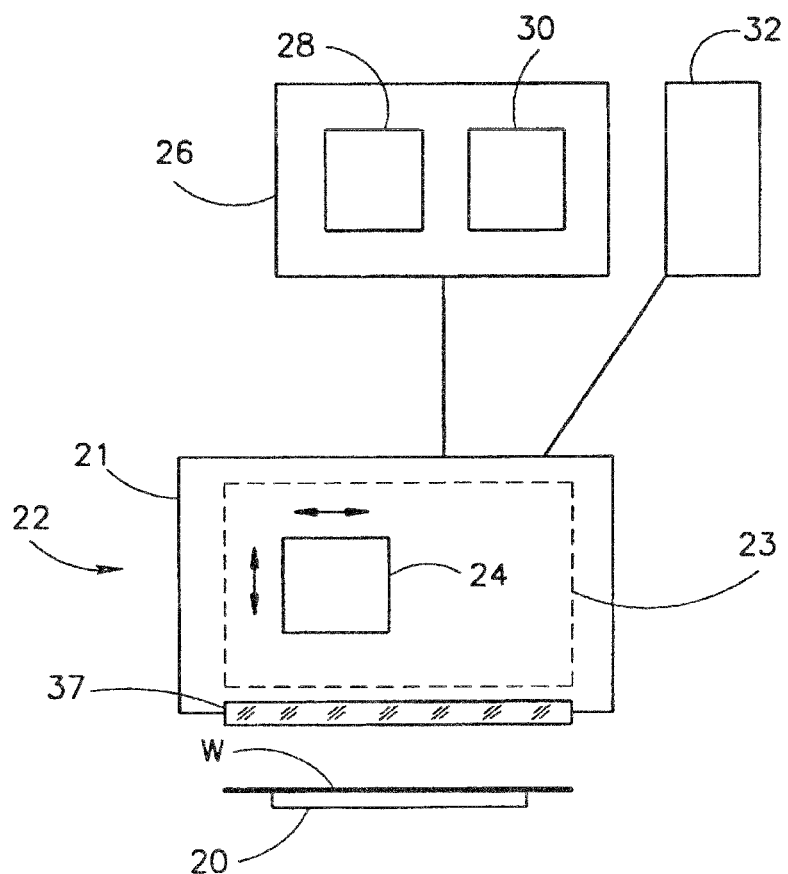
FIG. 7 is a schematic side view of an integrated lithography monitoring system in the apparatus of FIG. 6.

FIG. 7 is a side view of the ILM system 14 according to a preferred embodiment of the present invention. The ILM system includes a rigid and stable supporting means 20 which receives and holds the wafer W stationary. This can also be a vacuum supporting plate or a vacuum handler (not shown) which holds the wafer W stationary from its bottom (back) side. Supporting plate 20 is preferably located between the developing station DS and the unloading station US.

The ILM system 14 further includes a measuring unit (MU) 22 located above supporting means 20. The measuring unit 22 and supporting means 20 are rigidly mounted together in any suitable manner. As shown in FIG. 7, measuring unit 22 includes a sealed enclosure 21 with a transparent optical window 37 aligned with and facing the supporting plate 20 and optical unit inside the sealed enclosure 21, schematically indicated at 23 having a movable optical head 24. The wafer is illuminated via a source 32 which is externally of the sealed enclosure 21 and directs a beam to the measuring unit 22 via an optical fiber (not shown) passing into the sealed enclosure 21. As will be described more particularly below, movable optical head 24 enables the measuring unit 22 to perform any one of a number of preselected measurements on any preselected wafer W supported by plate 20 via transparent window 37.

As further shown in FIG. 7, the ILM system 14 further includes a control unit, generally designated 26, which is externally of the sealed enclosure 21 and is connected to the MU 22 by electrical conductors (not shown) passing into the sealed enclosure 21. Control unit 26 includes a central processing unit (CPU) 28, and optionally, an image processing unit (IPU) 30, as well as the electronic controls (not shown) for controlling the real time operation of the measuring unit 22.

Thus, in accordance with this preferred embodiment, the design of the ILM system 14 should meet several principles, including: (a) small size, (b) maintaining the wafer stationary during measurement, (c) rigid and stable measuring unit, (d) cleanness restrictions attained by, among other things, full separation of measuring unit 22 from the photocluster environment i.e., all moving parts are located within the sealed enclosure 21 of the unit 22 and external light source, (e) high speed measuring (e.g., fast scanning), and (f) easy and quick maintenance by, e.g., simple replacement of any one of the above mentioned units. It is also noted that the ILM system has the option to be bypassed by the production process and to be simultaneously operated in off-line or in integrated modes.

Figure 8:
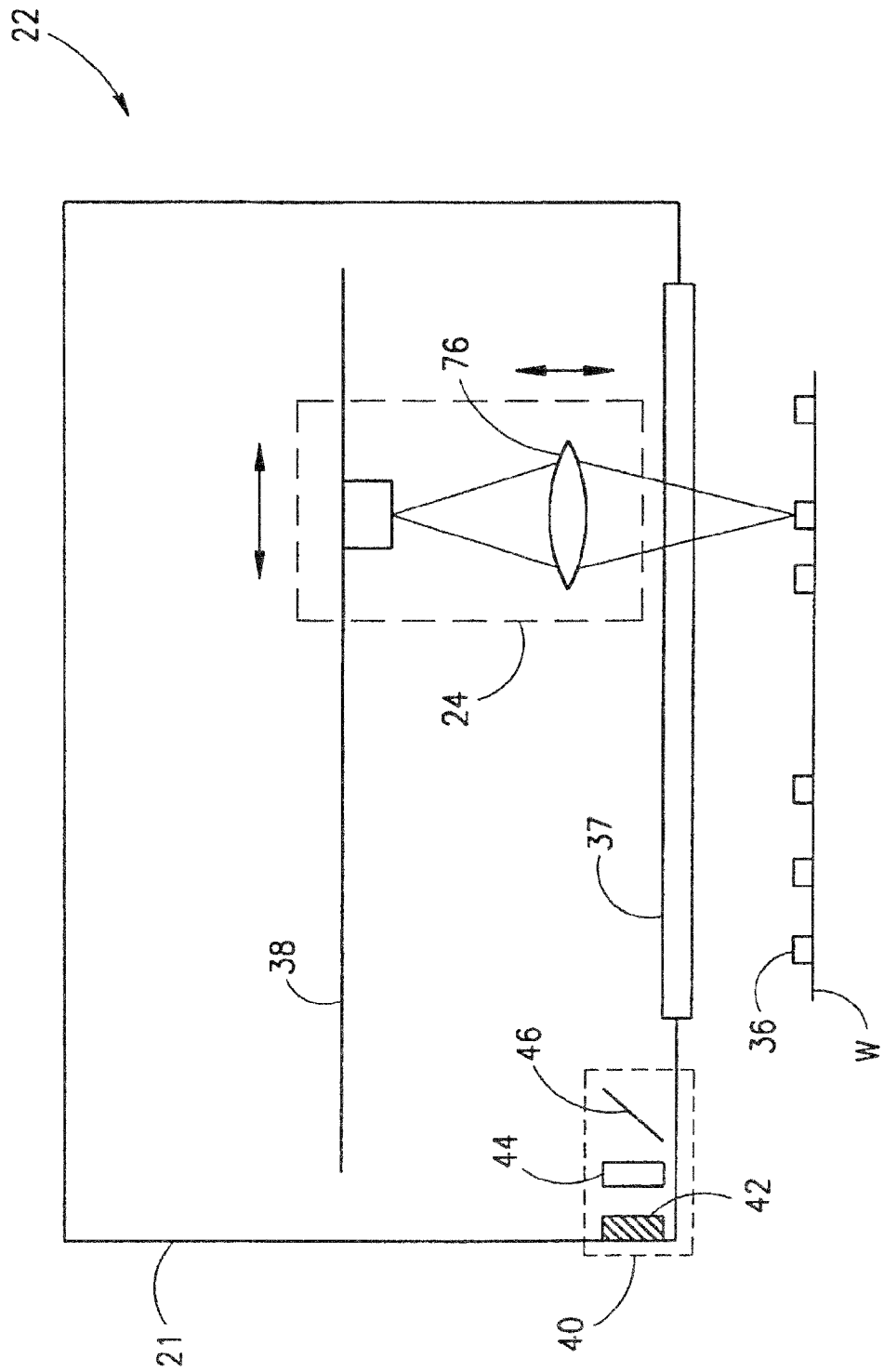
FIG. 8 is a schematic illustration of a preferred embodiment of the present invention used as an integrated overlay metrology tool.

FIG. 8 is a schematic illustration of the ILM system 14 according to a preferred embodiment of the present invention for measuring overlay registration errors. However, it should be noted that the hereinafter description is applicable as well to other preferred embodiments of the present invention such as an apparatus for defect inspecting, or for measuring OCD errors. The measuring unit 22 is shown in a measuring position, i.e., above a wafer W with a developed PR coating 36. The optical head 24 is able to move rapidly along x and y axis of an X-Y stage 38, and also along the vertical Z-axis. Between the optical head 24 and the wafer W there is the optical window 37 which prevents any potential disturbance or contamination to the photocluster tools from the measuring unit 22.

The measuring unit 22 further includes a calibrating unit 40 which simulates a measuring position for the optical head 24 when it is located above it. The calibrating unit 40 is composed of a target 42, a glass plate 44, and a mirror 46. The target 42 is any high contrast object, such as a metallic pattern on a glass substrate which is suitable for determining the line spread function of the optical system (e.g., a knife-edge pattern). The glass plate 44 is of the same material and thickness as optical window 37. The target is located in the object plane of objective 76 similar to where the wafer W is located.

Figure 9:
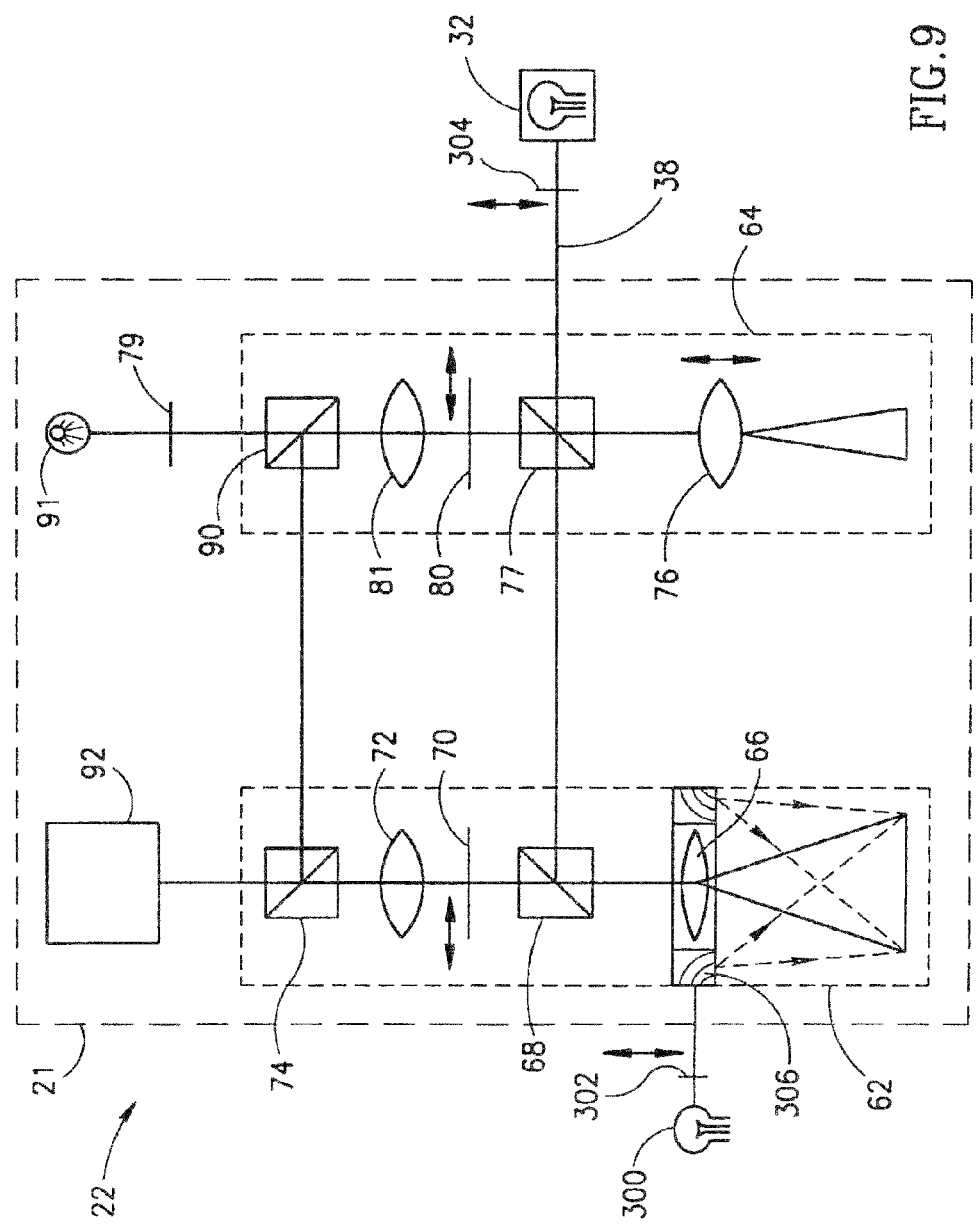
FIG. 9 is a schematic illustration of one form of optical system that may be used in this apparatus of the present invention.

FIG. 9 is a schematic illustration of the measuring unit 22 according to a preferred embodiment of the present invention as an overlay metrology tool. However, the illustrated optical configuration is applicable as well to other preferred embodiments of the present invention, such as for defect inspecting, or for OCD metrology, in a manner to be discussed later. As shown, the measuring unit 22 is composed of two alternative channels inside the sealed enclosure 21: (a) an alignment or low-magnification channel 62, and (b) a measuring or high-magnification channel 64. The low-magnification channel 62 is aimed at locating the optical head at the right position above an overlay target (FIG. 2) to be measured, whereas the high-resolution channel 64 is aimed at imaging the overlay target. In this embodiment, a single external white source light 32 and a single area CCD camera 92 serve both channels.

In another preferred embodiment of the present invention and for certain applications, a filter(s) is added (not shown) after light source 32 in order to produce a certain narrow spectral bandwidth which increases the contrast of the features to be measured.

The low-magnification channel 62 comprises an objective 66, a beam splitter 68, a shutter 70, a tube lens 72 and a beam splitter 74. Channel 62 has a relatively low-magnification power (e.g. 0.3-1.0×). The objective 66, which is part of the optical head 24 (FIG. 8), has a small numerical aperture and images a wide field of view (FOV) (e.g., 20-40 mm).

The high-magnification channel 64 comprises a vertically movable objective 76 which is part of the movable optical head 24 (FIG. 8), a beam splitter 77, a shutter 80, a tube lens 81, a beam splitter 90, a focus target 79, and LED illuminator 91. This channel has a relatively high-magnification power (e.g. ×20-100). The objective 76 has large numerical aperture since high resolution is needed and images a relatively small FOV (about 100 μm).

Figure 10:
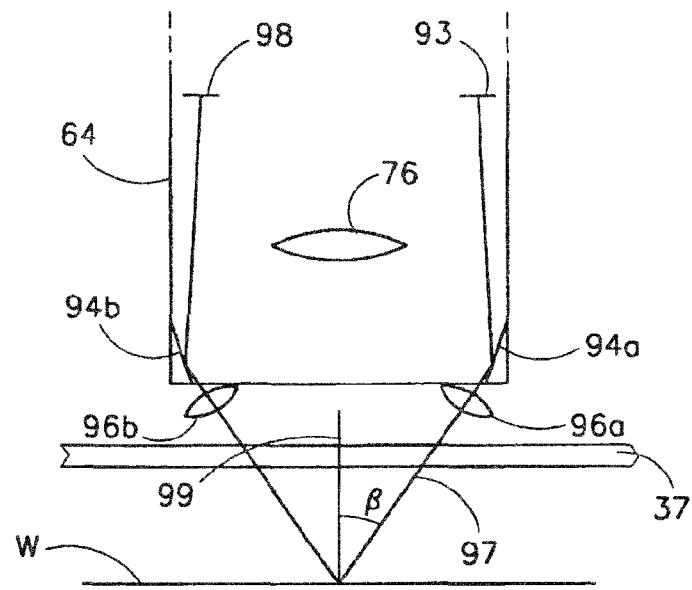
FIG. 10 is a schematic illustration of one manner that may be used for measuring the angle between the incident ray of the high-resolution channel to the wafer surface.

If higher accuracy is needed, measurement data correction may be achieved by determination of the actual incident angle of the illuminating light on the wafer's surface as illustrated in FIG. 10. The means for doing this is installed in the movable optical head 24 inside the high magnification channel 64 and comprise an LED 93, two identical mirrors 94*a* and 94*b*, two identical lenses 96*a* and 96*b*, and a position sensor (electronic) device 98 composed of single suitable photodiode or array of such photodiodes. The light from the LED 93 is reflected from the mirror 94*a* and is focused by lens 96*a* on the wafer at the same location where the light from the objective 76 is focused. From there, it is brought back through lens 96*b* and mirror 94*b* to the position sensor device 98. The position where the ray impulses the position sensor device 98 is translated by means of a function to the angle β between the objective's chief ray 99 and the ray 97. The measured angle β is introduced during a later step of image processing in order to correct the inaccuracies which may arise during measurement.

The focusing target 79 (FIG. 9.) is any high contrast object, such as a metallic pattern on a glass substrate. The pattern can be any easily identifiable pattern, such as a contrast edge, a grid, etc. It is installed in the optical path with the option of removing it when not needed (movable target), or of locating its image in the CCD plane 92 in such a way which does not interfere with the imaged wafer or imaged overlay targets. Other methods of focusing sensors can be applied as well.

A selection is needed to enable selection between operating the alignment channel 62 or the measuring channel 64. In this embodiment the selection is realized by shutters 70 and 80 which can be selectively opened or closed.

Figure 2B:
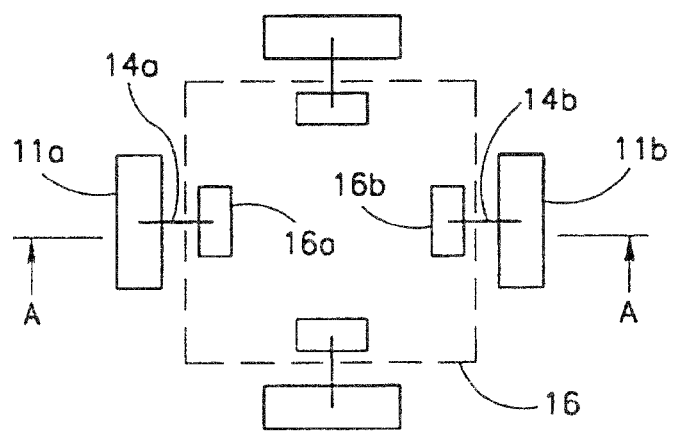
Figure 3:
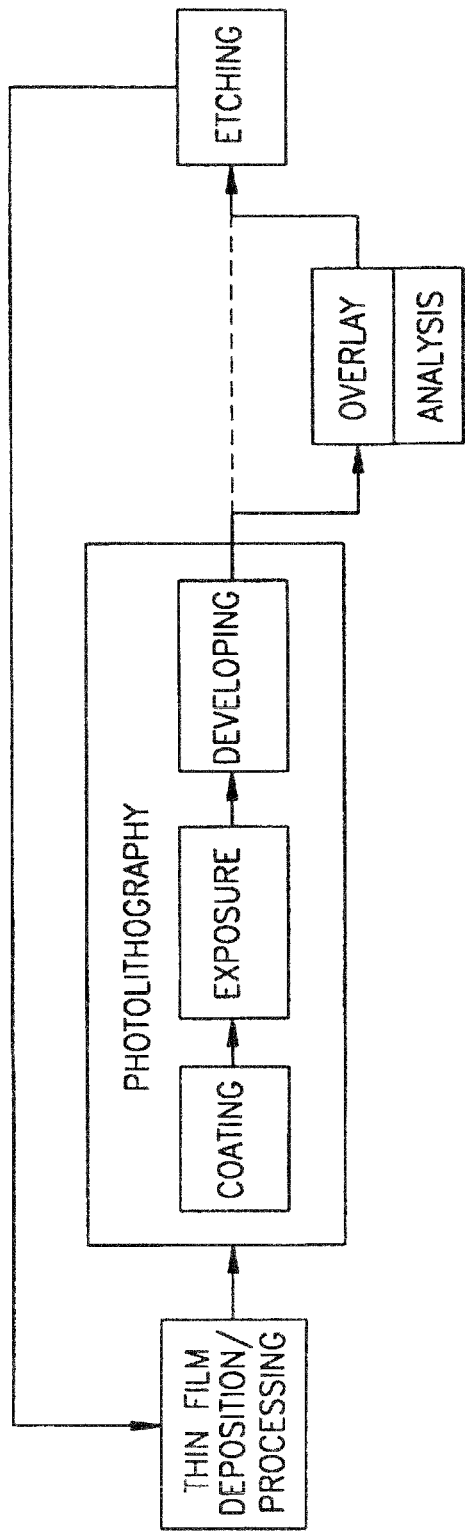
FIG. 3 is a block diagram illustrating a common configuration of photocluster tools and a 'stand-alone' overlay metrology system.
Figure 4:
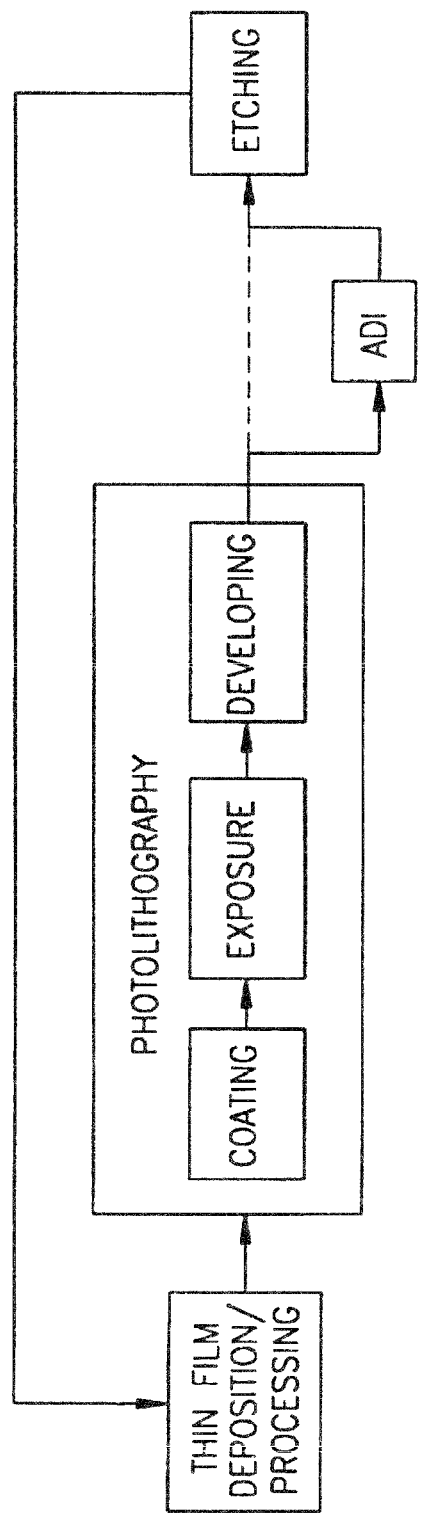
FIG. 4 is a block diagram illustrating possible points where after developing, inspecting can be introduced with respect to semiconductor multi-layer production process.
Figure 5:
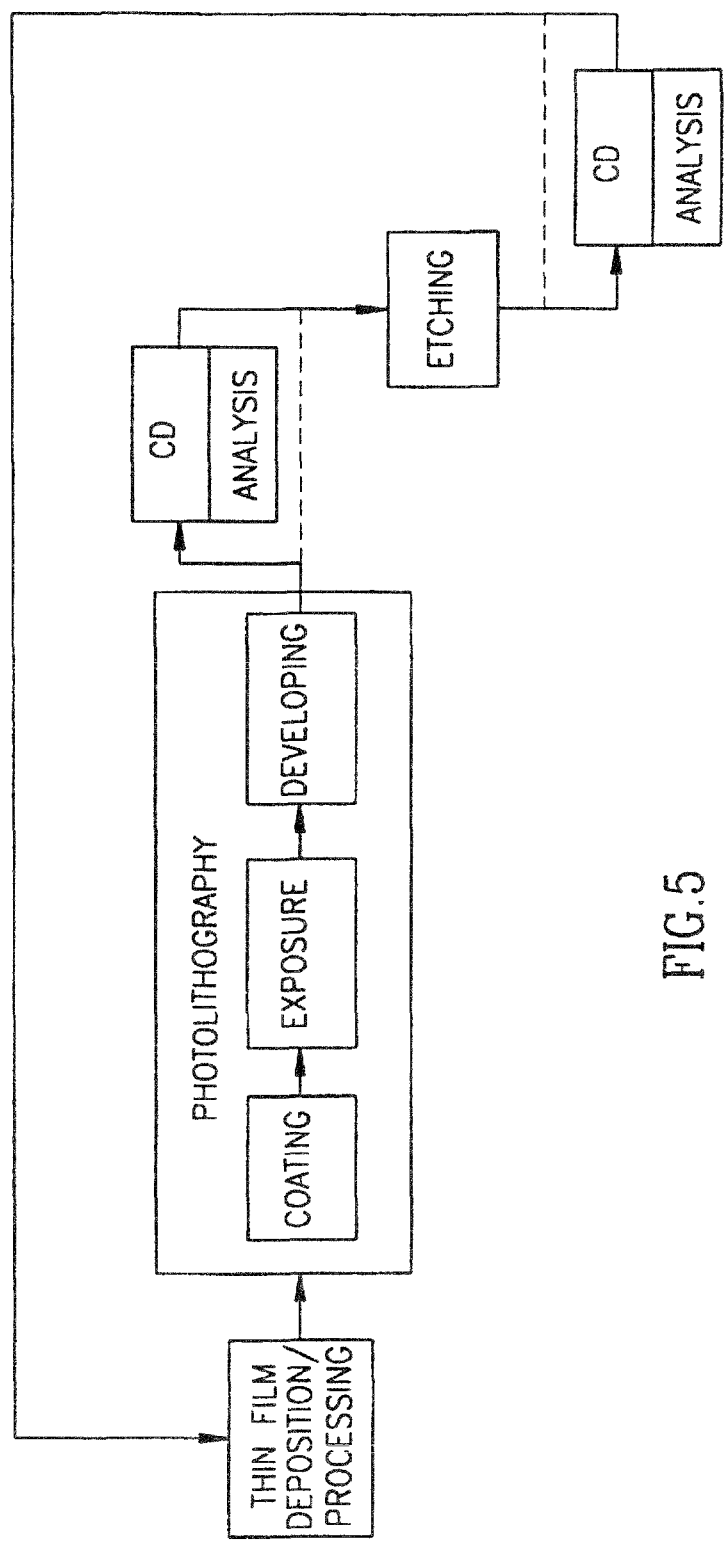
FIG. 5 is a block diagram illustrating common configurations of 'stand-alone' CD tools presently used in the production process.
Figure 11:
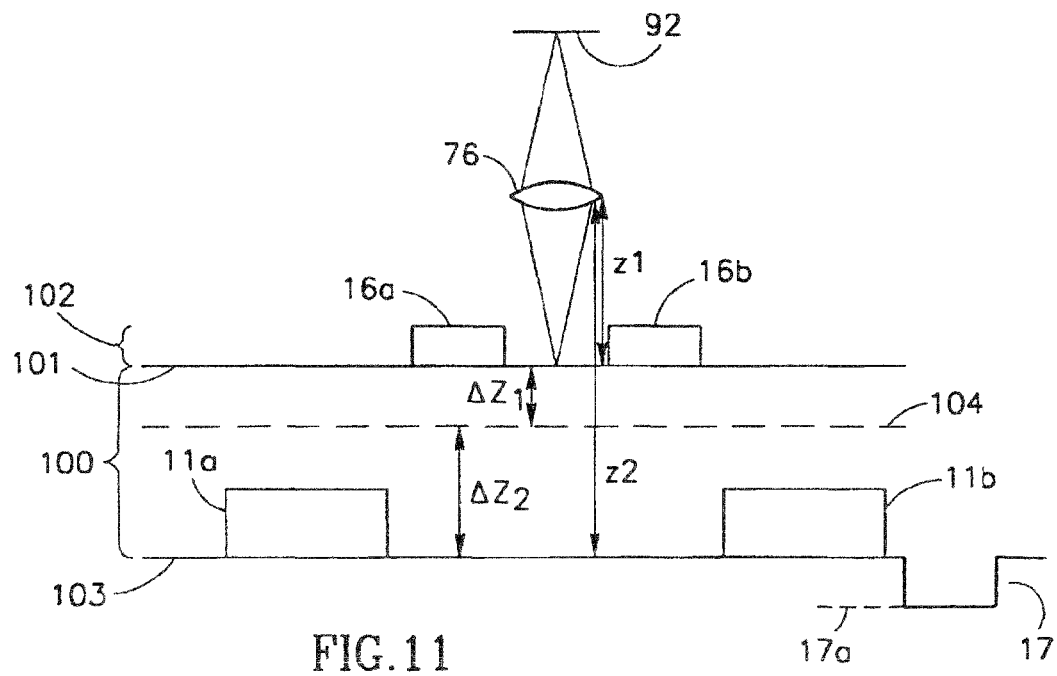
FIG. 11 is a view along the section lines A-A in FIG. 2B.

Reference now is made to FIG. 11 which is a side view along the section line A-A in FIG. 2B. FIG. 11 illustrates the uppermost features layer 100 on the wafer, and above it, the developed top PR layer 102. Layers 100 and 102 are separated by the interface 101, whereas layer 100 is separated from the layer below it (not shown) by interface 103. Layer 100 comprises the overlay target lines 11*a* and 11*b*, whereas PR layer 102 comprises the overlay target lines 16*a* and 16*b*.

The focusing procedure is aimed at locating, in a repetitive way, the object plane 104 of objective 76 of the measuring channel 64 at predetermined distances, $\Delta z_1$ and $\Delta z_2$, from interfaces 101 and 103, respectively. These distances are determined during the measurement program preparation for a certain product to be measured.

The focus condition of objective 76 over interface 101, indicated as $z_1$, in FIG. 11, is determined according to any known procedure, such as that disclosed in U.S. Pat. No. 5,604,344. In the same manner the objective 76 is additionally moved down in order to detect, in the same procedure, its exact location $z_2$ above interface 103. It should be noted that when the overlay target 17 on layer 100 is a 'negative' feature (e.g., a trench), instead of 'positive' feature such as 11*a*, it is possible to determine the focus plane 104 with respect to plane 17*a* instead of interface 103.

Once the locations $z_1$ and $z_2$ are known, the object plane 104 of objective 76 can be precisely located at distances $\Delta z_1$ and $\Delta z_2$ from interfaces 101 and 103 respectively. At this location, measuring takes place in order to produce an approximately equivalently defocused image of both target lines 11 and 16 onto the CCD's image plane 92.

Figure 12:
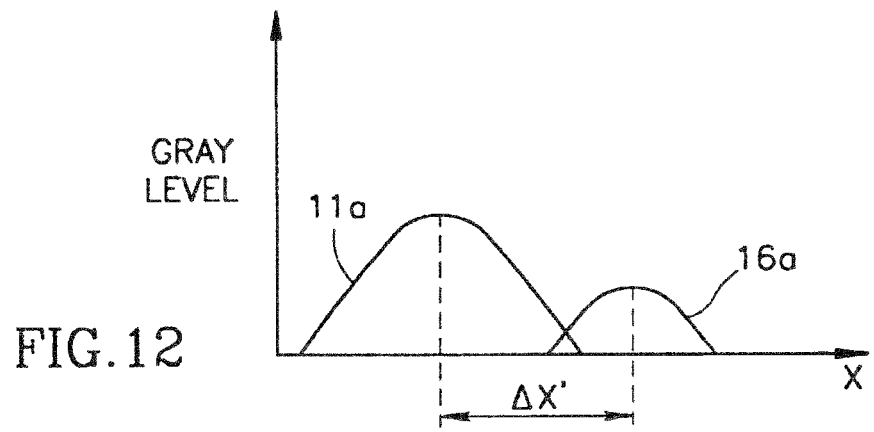
FIG. 12 is a schematic illustration of the gray level of target lines 11*a* and 16*a* (FIG. 11)

To calculate the overlay error, the exact locations of the centers of target lines 11*a*, 11*b*, 16*a*, and 16*b* should be determined. For this purpose, several alternative methods are known. It is noted that with respect to other types of overlay targets (e.g., multi-layer box, not shown) the same below-described methods can be used. One method is illustrated with the aid of FIG. 12 which shows the gray level of target lines 11*a* and 16*a* (FIG. 11) images. The gray levels are obtained by transforming the electrical signals of the CCD camera 92 (FIG. 9) into the digital form, e.g., by means of analogue-to-digital converter (not shown). The Central Processing Unit (CPU) 28 (FIG. 7) determines the centers of the gray levels lines 11*a* and 16*a*. The difference between these centers Δx expresses the length of line 14*a* (FIG. 2), depending on the magnification along the measuring and imaging channels. In a similar manner the length of line 14*b* is determined and the overlay error can be calculated for the x axis.

In the same manner, the overlay error can be calculated for the y-axis.

Figure 13A:
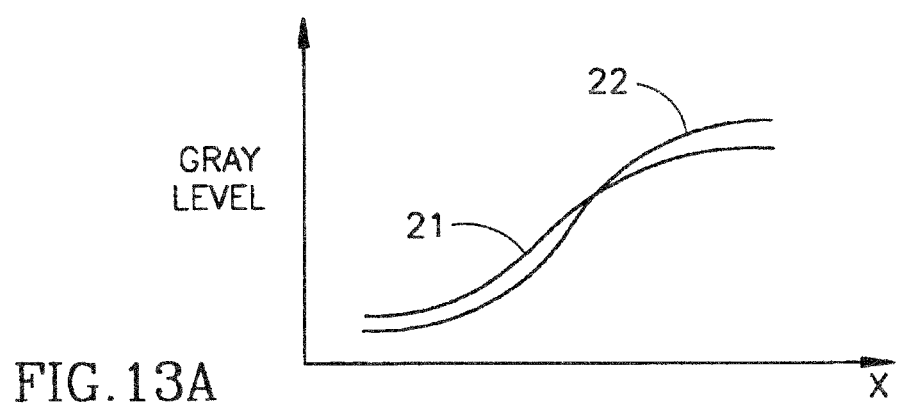
FIGS. 13A and 13B are schematic illustrations of the gray levels of images of a 'knife edge' pattern and their line spread function (LSF) functions.
Figure 13B:
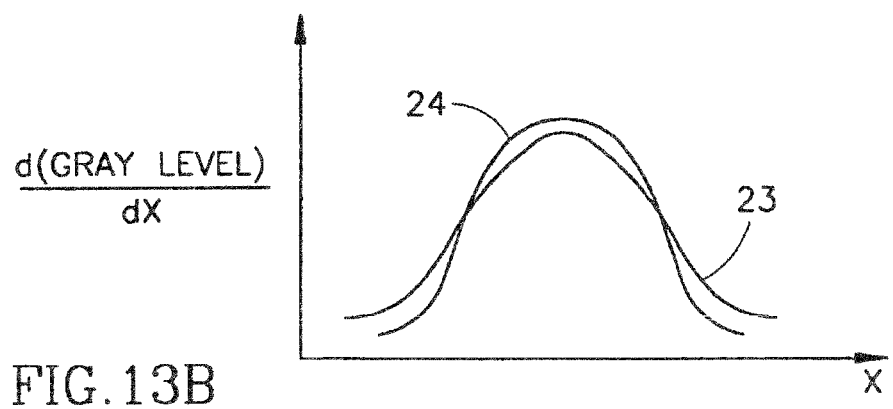

When the shapes of the gray levels 11*a* and 16*a* (FIG. 12) are not symmetrical with respect to the vertical axis, or are imperfect, the overlay error may be calculated using the line spread function (LSF) of the measuring channel. The LSF is accurately determined with the aid of the calibrating unit 40 (FIG. 8) at different heights above the calibrating target 42. FIG. 13 illustrates at "A" the gray levels of images of a 'knife edge' pattern on a calibrating target at two different heights 21 and 22 above the calibrating target 42. The derivatives of the gray levels 21 and 22 with respect to the x-axis are shown at "B", as 23 and 24, respectively, in FIG. 13. Now, by applying a de-convolution process the CPU 28 calculates the shape of the target line along the x axis. In order to compensate for the physical height of the target lines, de-convolution is conducted in at various locations along the target line profile (vertical axis) using the suitable LSF, as shown at "B" in FIG. 13 for each location. The target shape is determined from these profiles.

In the same manner, the shape of the target lines along the y axis can be determined, and the overlay error may be calculated.

In general, when the gray levels shapes 11*a* and 16*a* (FIG. 12) are not symmetrical with respect to the vertical axis, or are imperfect, a more complicated algorithm can be used, e.g., a comparison of the obtained gray levels of the target lines with their original shape and dimensions in the masks.

Figure 14:
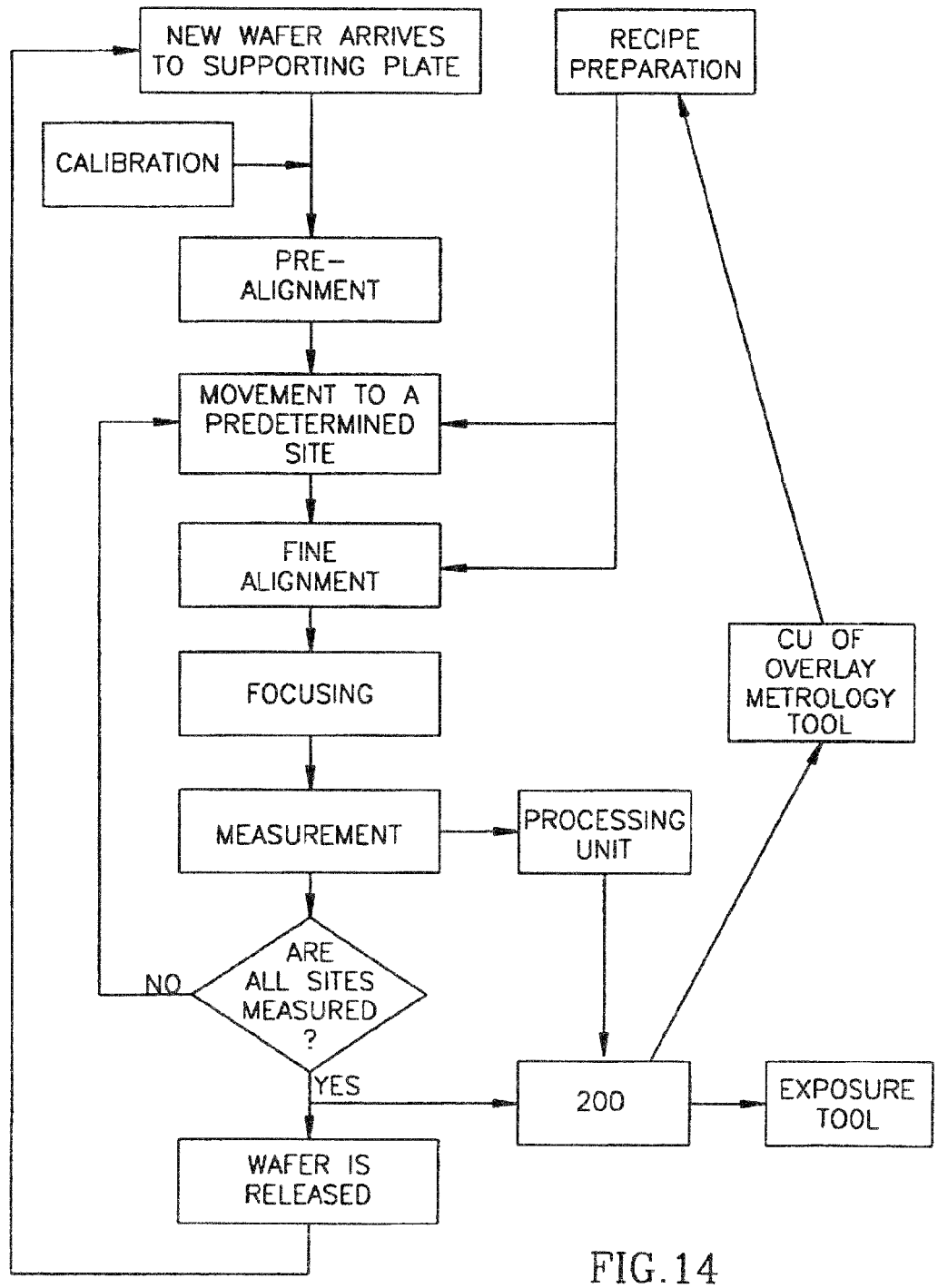
FIG. 14 is a schematic flow chart of a method to determine overlay error in accordance with a preferred embodiment of the present invention.

FIG. 14 is a schematic flow chart of a method to determine overlay error in accordance with a preferred embodiment of the present invention. After a new wafer to be measured arrives at the supporting plate 20 (FIG. 7), calibrating of the measuring system takes place and then the wafer is aligned with respect to its principle axis. After alignment, the optical head 24 moves to a pre-determined site on the wafer according to a previously prepared program. The program contains data which is relevant for operating the alignment 62 and measuring 64 channels (FIG. 9), such as recognized patterns of the overlay target onto the wafer and its coordinates. With the aid of the wide FOV of the alignment channel 62 (FIG. 9), and relevant data in the program, the optical head 24 is brought above the site area. Now, a final alignment commences in order to locate the optical head 24 in its exact position above the site. An example of a method for wafer alignment (practically achieving both objectives of pre- and fine alignments) based on its pattern features is disclosed in U.S. Pat. No. 5,682,242. Then, the shutter 70 (FIG. 9) enters the optical path and blocks the alignment channel. An auto-focusing mechanism in the optical head 24 focuses the objective 76 (FIG. 9) on the focus plane 104 (FIG. 11). The overlay targets are imaged on the CCD 92, and the data which was obtained is processed by the image processing unit 30 (FIG. 7) in order to determine the overlay error. If all the predetermined sites on the wafer are already measured, the wafer is released back to the phototrack 5, and a new wafer is brought to the supporting plate 20. If not, measurement of the next site on the wafer takes place.

It is noted that the overlay tool has various operational modes: (i) overlay error measurement; (ii) the same as in (i), and another measurement when the wafer is rotated 180°; (iii) the same as in (i) conducted on one wafer, and another measurement conducted on another wafer which is rotated 180° with respect to the first; (iv) overlay error is measured at different heights, and accuracy is determined by rotating the wafer.

According to another preferred embodiment of the present invention, the overlay error data which is determined by the processing unit, is transferred to a general control unit 200 (FIG. 14) of the photocluster, or of a specific tool in the photocluster. General control unit 200 uses this data for a feedback closed loop control to the exposure tool 8. It can also instruct the overlay metrology itself with respect to its operation (e.g., sampling frequency, site number to be measured on a wafer).

It will be appreciated that, by combining the processed data from the overlay system, with data of the defect inspecting process and of the OCD metrology, all within the same apparatus, an extensive integrated monitoring and control system for the photolithography process can be established. It will also be appreciated that overlay errors, defects and OCD errors can be determined during the production process itself, or after or before any predetermined step; and that all this can be done either on all wafers of a lot, or on several selected wafers in the same lot.

Figure 15:
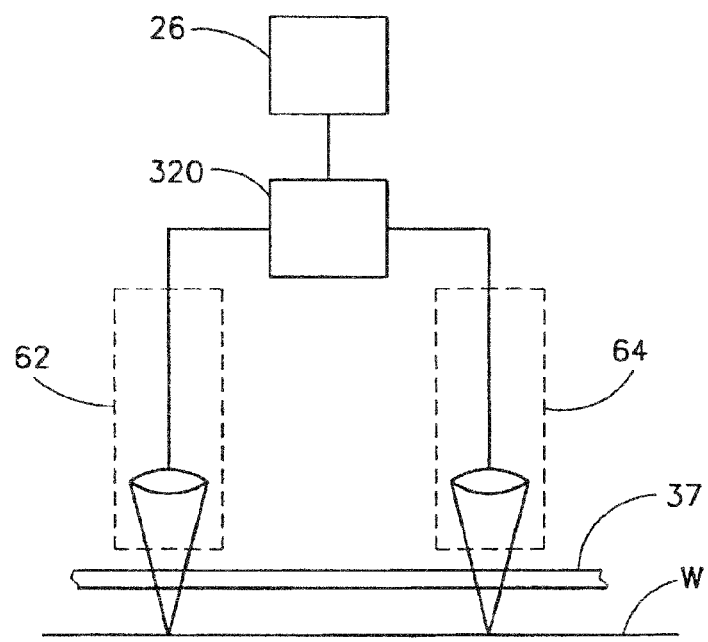
FIG. 15 is a schematic illustration of a preferred embodiment of the present invention as an inspecting tool.

FIG. 15 illustrates a preferred embodiment of the present invention configured as a defect inspecting tool.

The defect inspecting configuration is composed of: (a) two alternative optical channels, namely (1) a coarse inspecting channel 62 with a 0.3-3.0× magnification, and a (2) fine inspecting channel 64 with >20× magnification; (b) a fast image acquisition system 320; and (c) a processing unit 26. According to this embodiment, the inspecting tool is realized in the same overlay metrology, as described above.

With reference to the previously-described FIG. 9 which illustrates the main optical elements in the measuring unit 22, only a few optical elements need to be added in addition to those used in the overlay metrology system as described above to enable the apparatus also to be used for inspecting of defects. Thus, the same apparatus can serve both as an overlay metrology tool or as a defect inspecting tool. Obviously, the defect inspecting functions can be realized in a separate apparatus than the overlay metrology function.

The additional elements added to the measuring unit 22 of FIG. 9, for the defect inspecting function, include a light source 300, shutters 302 and 304 to block either the additional light source 300 or light source 32, and a ring light 306 which surrounds the objective 66. Ring light 306 has to produce a uniform light cone around the objective 66 with an opening angle of ca. 5-10°.

Figure 16:
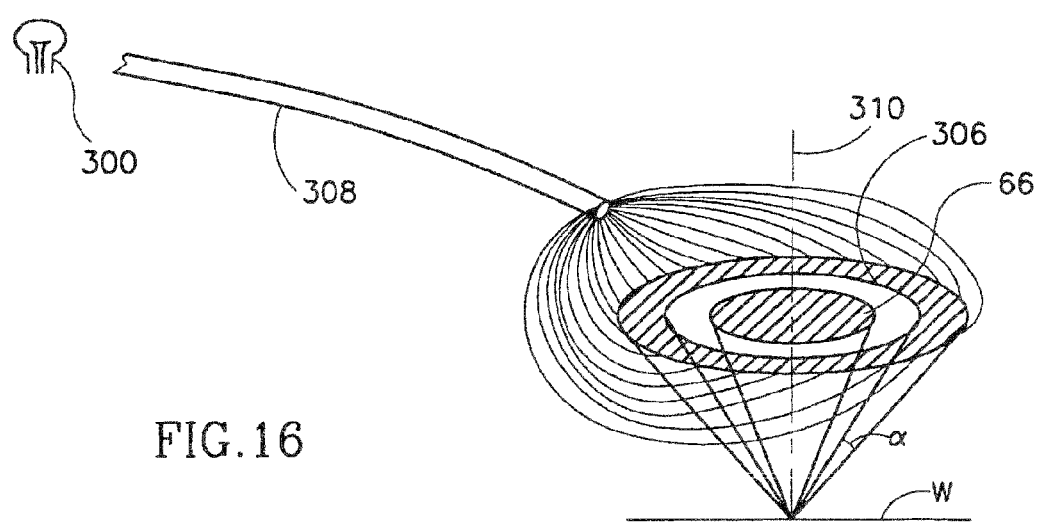
FIG. 16 is a schematic illustration of one way by which light from a light source may be conveyed to the ring light.

FIG. 16 illustrates how light from an external light source 300 is conveyed to the ring light 306. This is achieved by means of a bundle 308 of optic fibers passing through the sealed enclosure 21, wherein each single fiber leads its light to a certain location onto the ringlight. In the illustrated embodiment, ring light 306 is a fiber optic ring light. As an alternative, LEDs with narrow bandwidths could be used when placed along the ring light periphery. The ring light is aimed at producing a uniform light-cone with an opening angle larger than ca. 2° (α in FIG. 16) in order to cause diffracted non-specular light from the wafer W to fill the objective 66.

Alternatively, light 310 coming through objective 66 from light source 32 illuminates the wafer W and its specular component fills objective 66.

Thus, in this preferred embodiment, illumination and viewing methods for coarse inspecting 62 are alternatively bright (BF) and dark (DF) fields illuminations, using shutter means 302 and 304 to block either light source, or by turning on/off the electrical supply to the light source. The fine inspecting channel 64 is realized by BF illumination only.

It will be appreciated that illuminating and viewing, in general, can be realized by either BF or DF illuminations, all dependent on specific inspecting goals (e.g., defect type). Also during BF and/or DF illumination, for certain applications increased contrast can be realized for example, by additional filter(s) (not shown) after light sources 32 and 300, respectively, in order to produce a certain narrow bandwidth. Further, during DF illumination, and for certain applications, a better distinction between diffraction and scattering effects can be achieved, e.g., by alternating broad and narrow spectral band illumination.

The defect inspecting tool may be designed to meet the same principles described above with respect to an overlay metrology system.

Figure 17:
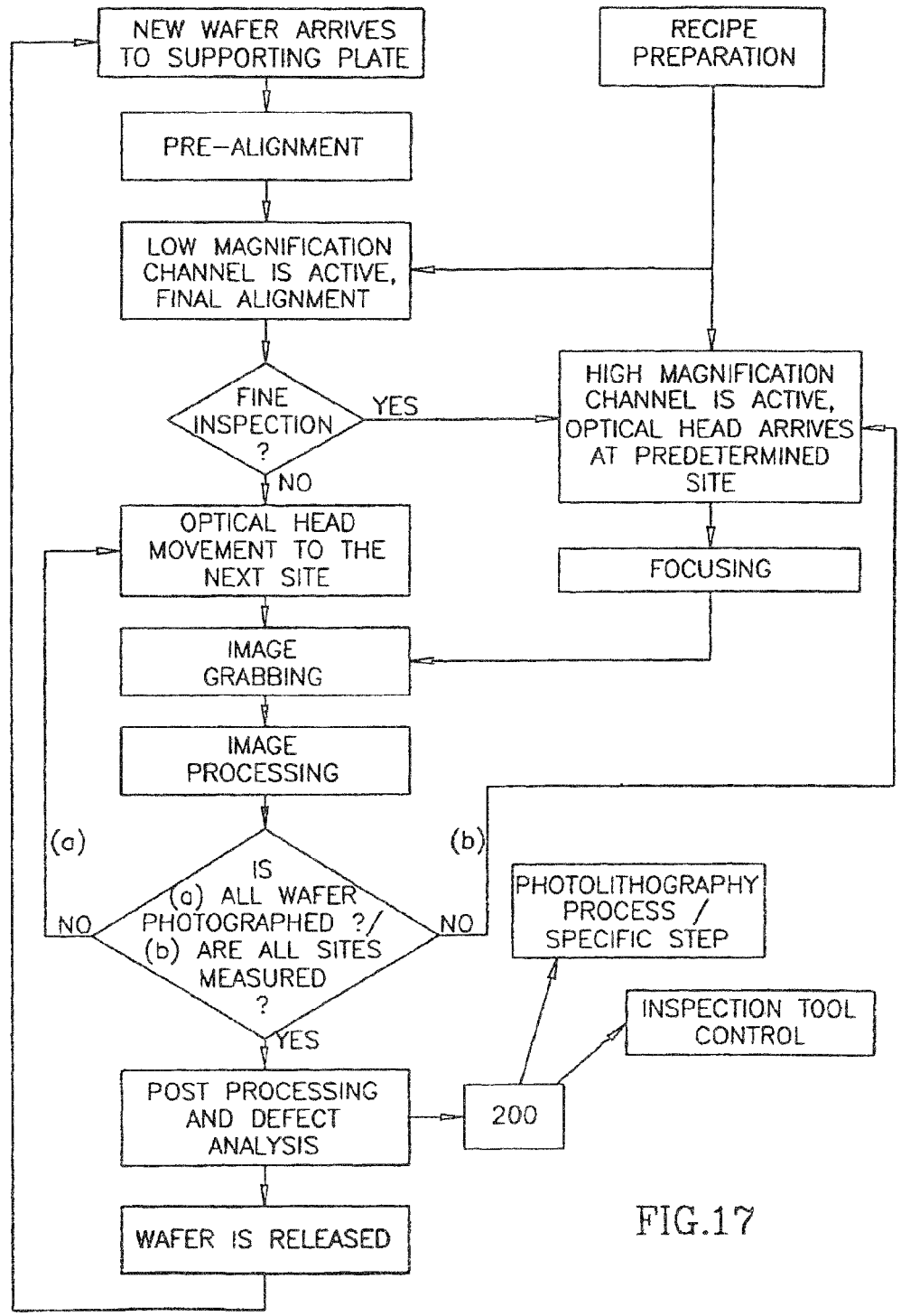
FIG. 17 is a schematic flow chart of a method for both coarse and fine inspecting in accordance with a preferred embodiment of the invention.

FIG. 17 is a schematic flow chart of a method for both coarse and fine inspecting in accordance with a preferred embodiment of the present invention.

After a new wafer to be measured arrives at the supporting plate, the wafer is pre-aligned with respect to its principle axis, in order to parallel the wafer's scribe lines and the CCD's lines. An example for a method for wafer's alignment disclosed in U.S. patent application Ser. No. 09/097,298. After pre-alignment, final alignment should take place, and a known method for this purpose based on its pattern features is disclosed in U.S. Pat. No. 5,682,242. With respect to fine inspecting, final alignment is aimed at fine correlation of the predetermined site to be inspected with its pattern stored already in the data base. Such data base is prepared, among other things, during recipe preparation.

After final alignment is conducted, image grabbing is performed during coarse inspecting in a step and repeat mode. According to this method, the optical head 24 moves to a predetermined area on the wafer, then stops and stabilizes and an image is grabbed. The procedure is repeated by moving to the next predetermined site usually used for wafer inspection.

According to the present invention, step and repeat procedure allows for a better performance than using a linear scanning method, e.g., raster scanning. During raster scanning, the wafer is continuously scanned and images are simultaneously grabbed. This method suffers from several drawbacks, such as reduced resolution and blurring along the movement axis, reduced resolution and inaccuracies due to non-stable velocity of the scanner, and non-efficient exploitation of the illumination system. During fine inspecting, images are grabbed at predetermined sites according to the recipe. At the next step, each image is processed in order to search for defects. This is performed either with absolute or comparative methods as known in the prior art. The processed data is stored in a data base. When the whole wafer complete a coarse inspecting, or all the predetermined sites are finely-inspected, post processing commences. Alternatively, post-processing may be conducted simultaneously. During post processing, the data can be evaluated and reported at different levels. This can be (a) defects list including numbers and coordinates of defects detected on the wafer, or (b) defects list including coordinates and defects dimensions, or (c) defects list including coordinates and defects identification, or (d) morphological defects analysis, e.g., according to local and/ or overall wafer distribution, such as radial distribution which may point on poor spinning during coating. This can be followed by (e) photographing certain defects for an additional processing; (f) attributing automatically defects to a certain problem source; (g) and reviewing options for correcting the defects (all or part). In addition, coarse and fine inspection can be combined. According to the processed results of the coarse inspection, fine inspection may be conducted in certain sites on a wafer where it is likely to find (e.g., based on thresholds) certain defects.

The post processing data, which is determined by the processing unit, may be transferred to a general control unit 200 of the photocluster tool. General control unit 200 may use this data for a feedback, or closed loop control, based on the level the data is processed (e.g., defect identification, or cause analysis). The feedback may be sent to the coating or other station which may affect the phototrack 5. The feedback may also instruct the inspecting metrology system itself with respect to its operation (e.g., sampling frequency, sites number to be measured on a wafer).

It is evident that these embodiments are superior to a parallel 'stand-alone' system in general, and to a visual inspecting system.

For certain occasions, where a more detailed inspecting is needed the ILM system 14 can be used as an off-line system so as not to disturb the production process.

According to another preferred embodiment of the present invention, the above-described overlay metrology system can also be used as OCD metrology system. The OCD metrology system as illustrated in FIG. 9 would contain the same channels 62 and 64 as the overlay metrology system, as well as the other optic elements. OCD determination would be executed in a similar way as overlay error determination as shown in FIG. 14 and discussed above. For this purpose, the optical head 24 (FIG. 9) would be moved to a predetermined site by the alignment channel 62, and then the measurement channel 64 would be operated in order to image the features to be measured.

Figure 18:
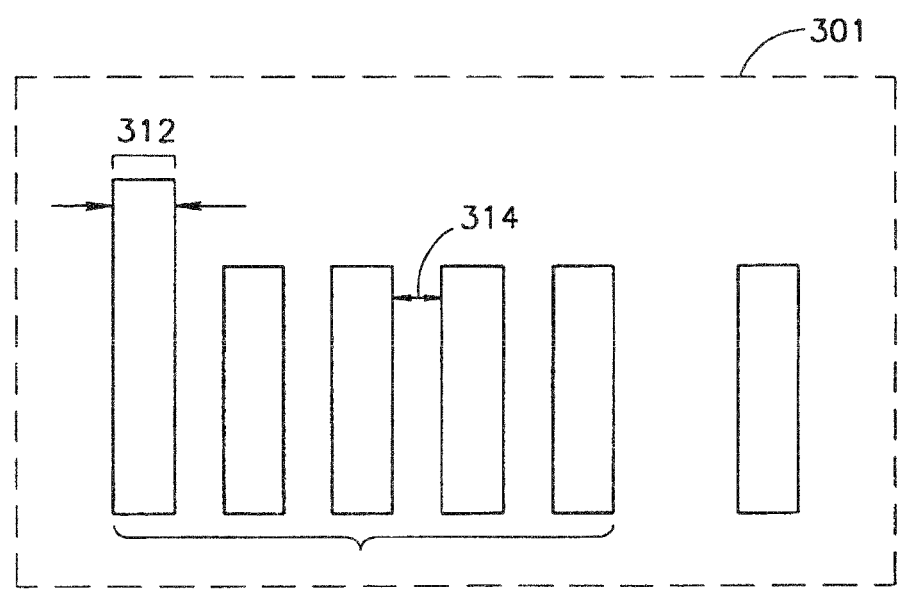
FIG. 18 is a schematic illustration of the field of view of the optical head during OCD measurement.

FIG. 18 illustrates the FOV 301 of the optical head 24 during measurement. In this example, the FOV contains two typical features to be measured: line width 312 and space 314. It is noted that according to this method for OCD determination, the FOV 301 should include a set of identical features to be measured. If this set is not part of the original features on the wafer, a test site which includes set(s) of such features should first be prepared.

Since the features to be measured are located in the same layer, focusing is conducted similarly to overlay measurements as described above, however, only with respect to one layer, except when features to be measured are in different layers. The feature's shape is reconstructed, in the same manner as for overlay, from its image using the LSF (x or y, z) of the optical system. The width of a space is determined by its adjacent lines edges which are reconstructed.

In this method, the width of the identical features in the set are determined, and by applying statistical calculations (e.g., mean value) the width of a representative feature is calculated. The accuracy of this measurement is based on the feature's degree of symmetry, the optical system, and the number of identical features to be measured. It is to be noted that usually, only the two latter parameters can be adjusted and prepared in advance, according to specific circumstances, in order to achieve the desired accuracy.

The monitoring and control based on OCD is established in the same manner described above with respect to overlay error determination.

Figure 19:
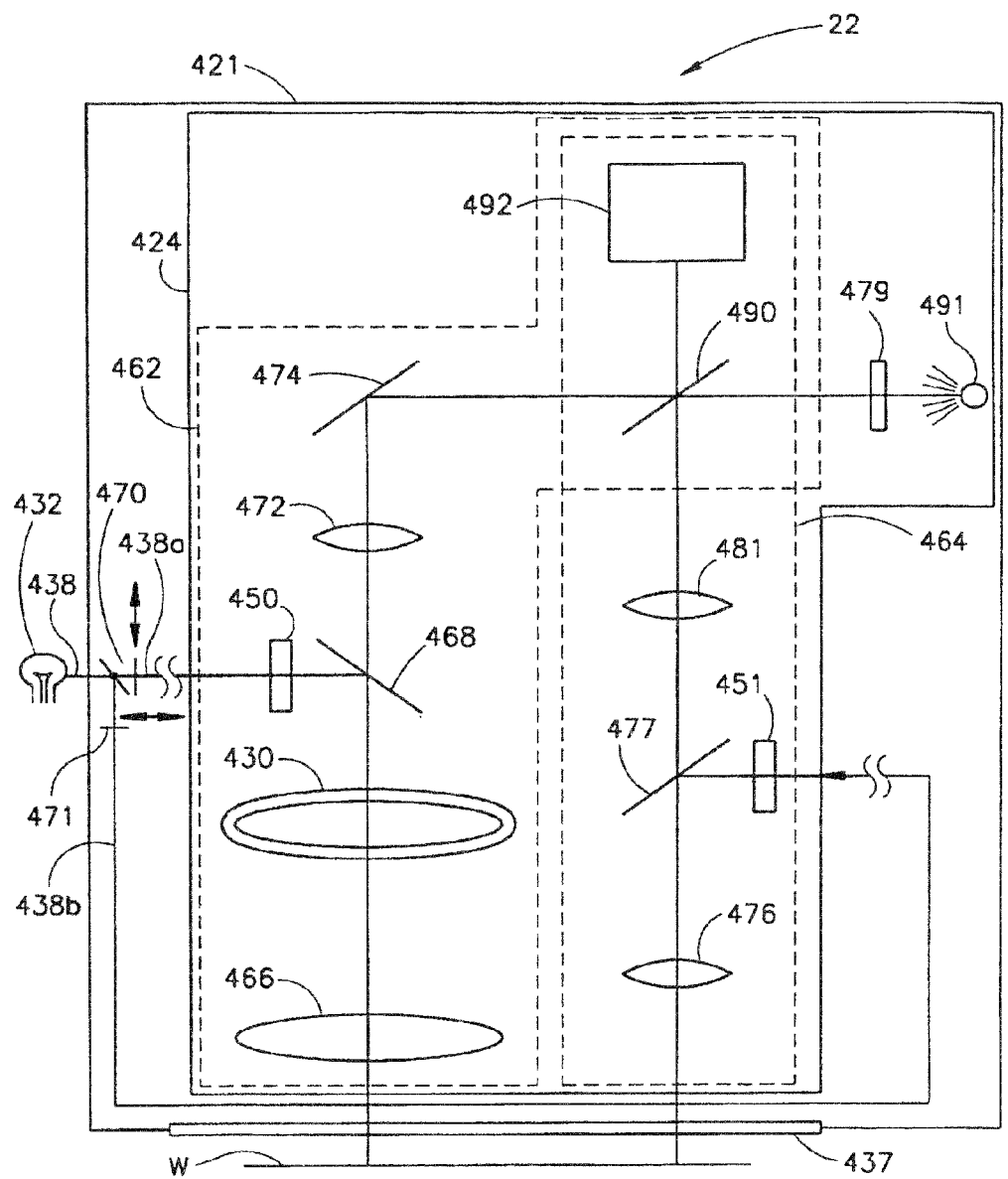
FIG. 19 is a schematic illustration corresponding to that of FIG. 9, but showing another form of optical system that may be used in the apparatus of the present invention.
Figure 20:
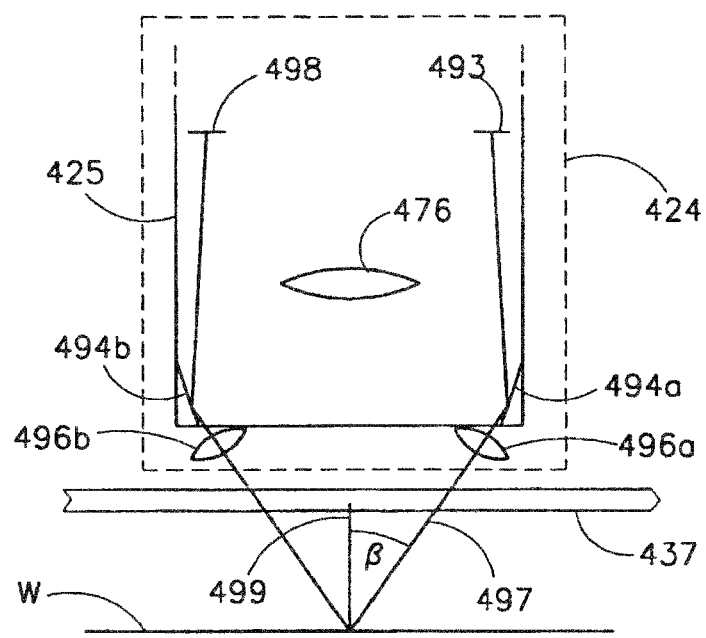
FIG. 20 is a schematic illustration, corresponding to FIG. 10, but showing a modification that may be included when the optical system of FIG. 19 is used.

FIG. 19 illustrates a modification in the optical system of FIG. 9; and FIG. 20 illustrates a modification in the system of FIG. 10 when using the optical system of FIG. 19. In this preferred embodiment, the internal configuration of FIG. 8 is slightly different. The MU 22 includes a sealed enclosure 421 with an optical window 437, where inside are installed the optical head 424 (modified according to FIGS. 19 and 20), the optical head's positioning means along x,y, axis 38 as well as along z axis, the calibrating unit 40, and additional electronic features and optic guides (not shown) which enable, respectively, external electric and light supply, as well as communications means (not shown) to the MU 22 with the CPU 28.

In the modified system of FIG. 19, the low-magnification channel 462, and the high-resolution channel 464, as well as the focusing target 479 and the LED 491 (corresponding to channels 62, 64, target 79 and LED 91 in FIG. 9) are contained within the movable optical head 424. It should be noted that the low-magnification channel 462 is used either for positioning the optical head 424 above a pre-selected site on a wafer to be measured during overlay, fine inspecting and OCD applications, or for coarse inspecting. The high-magnification channel 464 is used for measuring during overlay, OCD and fine inspecting applications.

Light from the external light source 432 is conveyed by optical fiber 438 and is split into two branches 438a, 438b, conveying the light into the sealed enclosures 421. Each of branches 438a and 438b is selectively controlled by shutters 470 and 471. Inside the sealed enclosure 421 the light from the two branches is conveyed by mirrors to the diffusers 450, 451 of the low-magnification channel 462 and the high-magnification channel 464, respectively.

The low-magnification channel 462 includes a field lens 466, a beam splitter 468, an imaging lens 472, a folding mirror 474, a beam splitter 490, and the CCD 492. The alignment channel 462 has a relatively low magnification power, (e.g., ×0.1-1.0.); and the imagining lens 472 has a small numerical aperture and images a wide field of view (e.g. 20-40 mm).

The high-magnification channel 464 comprises an objective 476, a beam splitter 477, a tube lens 481, a beam splitter 490, and the same CCD 492. This channel has a relatively high magnification power (e.g. ×20-100); and the objective 476 has a large numerical aperture since high resolution is needed.

In this preferred embodiment, DF illumination is realized by a ringlight 430 and light sources, e.g., LEDs, placed along the circumference of the ring light 430 and electric wires to operate the ring light 430. The ring light 430 is aimed at producing uniform light-cone with an opening angle larger than ca. 2° in order to cause diffracted non-specular light from the wafer w to fill the imaging lens 472. Light source 430 can be switched by turning on/off the electricity supply.

If higher accuracy during measurement is needed, a system similar to that illustrated in FIG. 10 may be used for accurately determines the actual angle between the optical axis 464 and the wafer surface W. FIG. 20 illustrates such a system which, in this case, is installed inside a housing 425 which surrounds the objective 476, and includes an LED 493, two identical mirrors 494a, 494b, two identical lenses 496a, 496b, and an electronic position sensor 498, corresponding to elements 76, 93, 94a, 94b, 96a, 96b, 98, respectively, illustrated in FIG. 10. The system in FIG. 20 can measure the angle β between the normal ray and the ray 497 from which the angle between the optical axis 499 and the wafer's plane can be determined.

The system of FIGS. 19 and 20 are otherwise constructed and operated in substantially the same manner as described above with respect to FIGS. 9 and 10, and utilize the focusing target 479 and calibration unit 40 for measuring channel 464.

Selection of the positioning mode of operation utilizing low-magnification channel 462, or the measuring mode of operation utilizing high-magnification channel 464, is realized by operating the mechanical shutters 470 and 471. The focused condition for the measuring channel 464 is determined according to known procedures, such as those described in the above-cited U.S. Pat. No. 5,604,344.

The modified optical system illustrated in FIG. 19 may also be used for determining overlay error in accordance with the flow chart schematically illustrated in FIG. 14. After a new wafer to be measured arrives at the supporting plate 20, calibration of the measuring system takes place by identifying a predetermined site on the wafer W, and locating the optical head 424 above it. The identification of a predetermined site may be based on the wafer pattern features, as disclosed in the above-cited U.S. Pat. No. 5,682,242.

The modified optical system illustrated in FIG. 19 may also be used for OCD measurements and inspecting in accordance with the flow chart schematically illustrated in FIG. 17.

While the invention has been described with respect to several preferred embodiments, it will be appreciated that these are set forth merely for purposes of example, and that many other variations, modifications and applications of the invention may be made.

What is claimed is:

1. A system for determining at least two properties of a substrate, comprising:
   a supporting plate configured to support the substrate;
   a measurement device coupled to the supporting plate, comprising
   an illumination system configured to direct light toward a surface of the substrate; and
   a detection system coupled to the illumination system and configured to detect light propagating from the surface of the substrate, wherein the measurement device is configured to generate one or more output signals in response to the detected light; and
   a control unit coupled to the measurement device and configured to determine a first property and a second property of the substrate from the one or more output signals, wherein the first property comprises a presence of macro defects on the substrate, and wherein the second property comprises overlay misregistration in the substrate.

2. The system of claim 1, wherein the supporting plate is further configured to move rotatably.

3. The system of claim 1, wherein the supporting plate is vacuum operated.

4. The system of claim 1, wherein the illumination system comprises a single light source.

5. The system of claim 1, wherein the illumination system comprises more than one light source.

6. The system of claim 1, wherein the detection system comprises a single light sensitive device.

7. The system of claim 4, wherein the detection system comprises a single light sensitive device.

8. The system of claim 1, wherein the measurement device comprises a bright field imaging device.

9. The system of claim 1, wherein the measurement device comprises a dark field imaging device.

10. The system of claim 1, wherein the measurement device comprises a bright field and dark field imaging device.

11. The system of claim 1, wherein the measurement device comprises at least first and second measurement channels including at least one of a bright field imaging device and a dark field imaging device.

12. The system of claim 1, wherein the measurement device comprises at least first and second measurement channels having common optical elements.

13. The system of claim 1, further configured to determine a third property from the one or more output signals, wherein the third property includes at least one of optical CD and micro defects.

14. The system of claim 1, configured to substantially simultaneously determine the at least two properties of the substrate.

15. The system of claim 1, configured to be integrated with a process tool.

16. The system of claim 15, being disposed within the process tool.

17. The system of claim 15, being attached to the process tool.

18. The system of claim 1, being coupled to a process tool, which comprises a substrate handler configured to move the substrate to the supporting plate.

19. The system of claim 1, being coupled to a process tool, and being configured to determine at least two properties of the substrate while the substrate is waiting between process steps.

20. The system of claim 1, being integrated with a process tool comprising a photolithography tool.

* * * * *